United States Patent
Wilson et al.

(10) Patent No.: US 11,135,313 B2
(45) Date of Patent: Oct. 5, 2021

(54) INTRATHECAL ADMINISTRATION OF ADENO-ASSOCIATED-VIRAL VECTORS FOR GENE THERAPY

(71) Applicant: The Trustees of the University of Pennsylvania, Philadelphia, PA (US)

(72) Inventors: James M. Wilson, Philadelphia, PA (US); Christian Hinderer, Philadelphia, PA (US); William Thomas Rothwell, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/771,481

(22) PCT Filed: Oct. 27, 2016

(86) PCT No.: PCT/US2016/058968
§ 371 (c)(1),
(2) Date: Apr. 27, 2018

(87) PCT Pub. No.: WO2017/075119
PCT Pub. Date: May 4, 2017

(65) Prior Publication Data
US 2018/0339065 A1 Nov. 29, 2018

Related U.S. Application Data

(60) Provisional application No. 62/247,498, filed on Oct. 28, 2015.

(51) Int. Cl.
*A61K 39/00* (2006.01)
*A61K 39/395* (2006.01)
*A61K 48/00* (2006.01)
*A61P 25/28* (2006.01)
*C07K 16/18* (2006.01)
*C12N 15/63* (2006.01)
*C12N 15/86* (2006.01)
*C07K 16/10* (2006.01)
*C12N 7/00* (2006.01)

(52) U.S. Cl.
CPC .......... *A61K 48/005* (2013.01); *A61K 39/395* (2013.01); *A61K 39/3955* (2013.01); *A61K 48/00* (2013.01); *A61P 25/28* (2018.01); *C07K 16/1063* (2013.01); *C07K 16/18* (2013.01); *C12N 7/00* (2013.01); *C12N 15/63* (2013.01); *C12N 15/86* (2013.01); *A61K 2039/54* (2013.01); *C07K 2317/622* (2013.01); *C07K 2317/71* (2013.01); *C12N 2750/14143* (2013.01)

(58) Field of Classification Search
CPC .. A61K 39/00; A61K 39/0007; A61K 39/395; A61K 39/3955; A61K 2039/51; A61K 2039/5256; A61K 2039/54; A61K 48/00; A61K 48/005; A61P 1/00; A61P 25/00; A61P 25/28; C07K 16/00; C07K 16/16; C07K 2317/622; C12N 15/63; C12N 15/86; C12N 15/8645; C12N 2750/14141; C12N 2750/14143
See application file for complete search history.

(56) References Cited

U.S. PATENT DOCUMENTS

| 5,139,941 | A | 8/1992 | Muzyczka et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,946,292 | B2 | 9/2005 | Kanda et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,198,951 | B2 | 4/2007 | Gao et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |

(Continued)

FOREIGN PATENT DOCUMENTS

| WO | WO-2003/042397 | 5/2003 |
| WO | WO-2005/033321 | 4/2005 |

(Continued)

OTHER PUBLICATIONS

Robert et al, Archives Biochem. Biophys. 526:132-138, 2012.*
Kou et al, Alzheimer's & Dementia 9(4): Abstract P2-407, P507, Jul. 1, 2013.*
Kou et al, Molecular Neurobiol. 51: 43-56, 2015; available online Apr. 15, 2014.*
Jinghong, Alzheimer's & Dementia: The Journal of the Alzheimer's Association, Expression of an anti-beta-amyloid catalytic antibody by AAV9-mediated gene delivery effictively prevents and reduces amyloid deposition in an Alzheimer's disease mouse model, vol. 9(4):507, Jul. 2013.

(Continued)

*Primary Examiner* — Kevin K Hill
(74) *Attorney, Agent, or Firm* — Howson & Howson LLP; Cathy A. Kodroff

(57) ABSTRACT

A composition comprising at least one AAV vector formulated for intrathecal delivery to the central nervous system is described. The composition comprises at least one expression cassette which contains sequences encoding an immunoglobulin construct linked to expression control sequences therefor and a pharmaceutically acceptable carrier. The immunoglobulin construct may be an immunoglobulin modified to have decreased or no measurable affinity for neonatal Fc receptor (FcRn).

8 Claims, 1 Drawing Sheet

Specification includes a Sequence Listing.

(56) References Cited

U.S. PATENT DOCUMENTS

| | | | |
|---|---|---|---|
| 7,588,772 | B2 | 9/2009 | Kay et al. |
| 7,790,449 | B2 | 9/2010 | Gao et al. |
| 7,906,111 | B2 | 3/2011 | Wilson et al. |
| 8,425,910 | B2 | 4/2013 | Mi et al. |
| 8,618,252 | B2 | 12/2013 | Farrington et al. |
| 9,909,142 | B2 | 3/2018 | Yazicioglu et al. |
| 2006/0136184 | A1 | 6/2006 | Gustafsson et al. |
| 2011/0236353 | A1 | 9/2011 | Wilson et al. |
| 2013/0045186 | A1 | 2/2013 | Gao et al. |
| 2013/0216555 | A1* | 8/2013 | Nitsch ............ G01N 33/6854 424/172.1 |
| 2014/0032186 | A1 | 1/2014 | Gustafsson et al. |
| 2014/0124086 | A1 | 5/2014 | Jean et al. |

FOREIGN PATENT DOCUMENTS

| | | |
|---|---|---|
| WO | WO-2006/110689 | 10/2006 |
| WO | WO-2007/012924 | 2/2007 |
| WO | WO-2011/126808 | 10/2011 |
| WO | WO-2013/004943 | 1/2013 |
| WO | WO-2013/046704 | 4/2013 |
| WO | WO-2013/155222 | 10/2013 |
| WO | WO 14/089500 * | 6/2014 |
| WO | WO-2014/089500 | 6/2014 |
| WO | WO-2015/012924 | 1/2015 |
| WO | WO-2015/120233 | 8/2015 |
| WO | WO 2015/120280 A1 | 8/2015 |
| WO | WO PCT/US2016/058968 | 4/2017 |

OTHER PUBLICATIONS

Jinghong, Molecular Neurobiology, Catalytic Immunoglobulin Gene Delivery in a Mouse Model of Alzheimer's Disease: Prophylactic and Therapeutic Applicat, vol. 51(1):43-56, Apr. 2014.

Bourdenx, Frontiers in Molecular Neuroscience, Systemic gene delivery to the central nervous system using adeno-associated virus, vol. 7:1-8, Jun. 2014.

Cardinale, International Journal of Cell Biology, Gene-Based Antibody Strategies for Prion Diseases, vol. 12(2):240-246, Jan. 2013.

Salegio et al., Frontiers in Neuroanatomy, Distribution of nanoparticles throughout the cerebral cortex of rodents and non-human primates: implications for gene and drug therapy, vol. 8:1-8, Mar. 2014.

Meyer et al., Molecular Therapy, Improving Single Injection CSF Delivery of AAV9-mediated Gene Therapy for SMA: A Dose-response Study in Mice and Nonhuman Primates, vol. 23(3):477-487, Mar. 2015.

Hinderer et al., Molecular Therapy, Widespread gene transfer in the central nervous system of cynomolgus macaques following delivery of AAV9 into the cisterna magna, vol. 1(1):14051, Jan. 2014.

Zincarelli et al, Molecular Therapy, Analysis of AAV Serotypes 1-9 Mediated Gene Expression and Tropism in Mice After Systemic Injection, vol. 16(6):1073-1080, Jun. 2008.

Maguire-Zeiss et al., Journal of Neuroimmune Pharmacology, Immune-Directed Gene Therapeutic Development for Alzheimer's, Prion, and Parkinson's Diseases, vol. 4(3):298-308, Oct. 2008.

Kantor et al., Advances in Genetics, Clinical Applications Involving CNS Gene Transfer, vol. 87:71-124, Jan. 2014.

Jingfeng et al., Cancer Letters, Adeno-associated virus-mediated cancer gene therapy: Current status, vol. 356(2):347-356, Nov. 2014.

Bourdenx et al., Systemic gene delivery to the central nervous system using adeno-associated virus, Frontiers in Molecular Neuroscience, vol. 7:1-8, Jun. 2014.

Brody and Holtzman, Active and Passive Immunotherapy for Neurodegenerative Disorders, Annu Rev Neurosci, vol. 31:175-193, Oct. 2008.

Cardinale et al., Gene-Based Antibody Strategies for Prion Diseases, International Journal of Cell Biology, vol. 12(2):240-246, Jan. 2013.

Edelman et al., The Covalent Structure of an Entire rG Immunoglobulin Molecule, Proc. Natl. Acad. USA, vol. 63:78-85, Mar. 1969.

Gao et al, Clades of Adeno-Associated Viruses Are Widely Disseminated in Human Tissues, J. Virol, vol. 78:6381-6388, Jun. 2004.

Gao, et al, Adeno-associated viruses undergo substantial evolution in primates during natural infections, Proc. Natl. Acad. Sci. U.S.A., vol. 100(10):6081-6086, May 2003.

GenBank Accession No. AAS99264, apsid protein VP1 [Adeno-associated virus 9], Jun. 2004.

Glamann et al. Characterization of a Macaque Recombinant Monoclonal Antibody That Binds to a CD4-Induced Epitope and Neutralizes Simian Immunodeficiency Virus, J Virol, vol. 74(15):7158-7163, Aug. 2000.

Greig et al., Intramuscular Injection of AAV8 in Mice and Macaques Is Associated with Substantial Hepatic Targeting and Transgene Expression, PLoS ONE, vol. 9(11): e112268, Nov. 2014.

Hinderer et al., Widespread gene transfer in the central nervous system of cynomolgus macaques following delivery of AAV9 into the cisterna magna, Molecular Therapy, vol. 1(1):14051, Jan. 2014.

International Nonproprietary Names for Pharmaceutical Substances (INN), WHO Drug Information, vol. 27, No. 4, pp. 401-402, Jan. 2013.

International Nonproprietary Names for Pharmaceutical Substances (INN), WHO Drug Information, vol. 25, No. 2, pp. 163-164, Jan. 2011.

International Nonproprietary Names for Pharmaceutical Substances (INN), WHO Drug Information, vol. 23, No. 3, pp. 263-264, Jan. 2009.

Jingfeng et al., Adeno-associated virus-mediated cancer gene therapy: Current status, Cancer Letters, vol. 356(2):347-356, Nov. 2014.

Jinghong et al., Catalytic Immunoglobulin Gene Delivery in a Mouse Model of Alzheimer's Disease: Prophylactic and Therapeutic Applicat, Molecular Neurobiology, vol. 51(1):43-56, Apr. 2014.

Jinghong et al., Expression of an anti-beta-amyloid catalytic antibody by AAV9-mediated gene delivery effectively prevents and reduces amyloid deposition in an Alzheimer's disease mouse model, Alzheimer's & Dementia: The Journal of the Alzheimer's Association, vol. 9(4):507, Jul. 2013.

Kantor et al., Clinical Applications Involving CNS Gene Transfer, Advances in Genetics, vol. 87:71-124, Jan. 2014.

Lock et al, Absolute Determination of Single-Stranded and Self-Complementary Adeno-Associated Viral Vector Genome Titers by Droplet Digital PCR, Hu Gene Therapy Methods, vol. 25(2):115-25, Apr. 2014 (ePub Feb. 2014).

Maguire-Zeiss et al., Immune-Directed Gene Therapeutic Development for Alzheimer's, Prion, and Parkinson's Diseases, Journal of Neuroimmune Pharmacology, vol. 4(3):298-308, Oct. 2008.

Matsushita, Engineered therapeutic antibodies with enhanced effector functions: Clinical application of the Potelligent® Technology, Korean J Hematol, vol. 46(3):148-150, Sep. 2011.

McCarty et al., Self-complementary recombinant adeno-associated virus (scAAV) vectors promote efficient transduction independently of DNA synthesis, Gene Therapy, vol. 8(16):1248-1254, Aug. 2001.

McGoldrick et al., Rodent models of amyotrophic lateral sclerosis, Biochimica et Biophysica Acta (BBA)—Molecular Basis of Disease, vol. 1832(9):1421-1436, Sep. 2013.

Meyer et al., Improving Single Injection CSF Delivery of AAV9-mediated Gene Therapy for SMA: A Dose-response Study in Mice and Nonhuman Primates, Molecular Therapy, vol. 23(3):477-487, Mar. 2015.

Moser et al., The wobbler mouse, an ALS animal model, Mol Genet Genomics, vol. 288(5-6):207-29, Jun. 2013 (ePub Mar. 2013).

Muzyczka, Use of Adeno-Associated Virus as a General Transduction Vector for Mammalian Cells, Current Topics in Microbiology and Immunology, vol. 158:97-129, Jan. 1992.

Patel et al., Adeno-associated Virus—mediated Delivery of a Recombinant Single-chain Antibody Against Misfolded Superoxide Dismutase for Treatment of Amyotrophic Lateral Sclerosis, Molecular Therapy, vol. 22(3):498-510, Mar. 2014.

Radcliffe and Mitrophanous, Multiple gene products from a single vector: 'self-cleaving' 2A peptides, Gene Therapy, vol. 11:1673-1674, Jan. 2004.

(56) References Cited

OTHER PUBLICATIONS

Rutting et al., Mutations in the carboxy terminus of adeno-associated virus 2 capsid proteins affect viral infectivity: lack of an RGD integrin-binding motif, J Gen Virol, vol. 75:3385-3392, Jul. 1994.
Salegio et al., Distribution of nanoparticles throughout the cerebral cortex of rodents and non-human primates: implications for gene and drug therapy, Frontiers in Neuroanatomy, vol. 8:1-8, Mar. 2014.
Srivastava et al., Nucleotide Sequence and Organization of the Adeno-Associated Virus 2 Genome J Virol, vol. 45(2):555-564, Feb. 1983.
Thomson et al, A comprehensive comparison of multiple sequence alignments, Nucl. Acids. Res., vol. 27(13):2682-2690, May 1999.
Tran et al, Cell Reports, α-Synuclein Immunotherapy Blocks Uptake and Templated Propagation of Misfolded α-Synuclein and Neurodegeneration, vol. 7(6):2054-2065, Jun. 2014.
Van Dam and De Deyn, Animal models in the drug discovery pipeline for Alzheimer's disease, Br J Pharmacol, vol. 164(4):1285-1300, Oct. 2011.
Webster et al., Using mice to model Alzheimer's dementia: an overview of the clinical disease and the preclinical behavioral changes in 10 mouse models, Front Genet. vol. 5:88, Apr. 2014.
Zhang et al., Adenovirus-adeno-associated virus hybrid for large-scale recombinant adeno-associated virus production, Human Gene Therapy, vol. 20:922-929, Sep. 2009.
Zincarelli et al, Analysis of AAV Serotypes 1-9 Mediated Gene Expression and Tropism in Mice After Systemic Injection, Molecular Therapy, vol. 16(6):1073-1080, Jun. 2008.
International Search Report and Written Opinion issued on International Patent Application No. PCT/US2016/058968, dated Apr. 18, 2017.
U.S. Appl. No. 62/247,498, filed Oct. 28, 2015.
International Application No. PCT/US15/30533, filed May 13, 2015.
International Application No. PCT/US15/27491, filed Apr. 24, 2015.
Hinderer C et al., Evaluation of Intrathecal Routes of Administration for Adeno-Associated Viral Vectors in Large Animals, 2018, Human Gene Therapy, 29 (1):15-24.
Weiner HL et al, Immunology and immunotherapy of Alzheimer's disease, Nature Reviews, Immunology, vol. 6:404-416, May 2006.
Sterniczuk R et al., Characterization of the 3xTg-AD mouse model of Alzheimer's disease: part 1. Circadian changes, Brain Res. vol. 12(1348):139-48, Aug. 2010 (ePub May 2010).
Sterniczuk R et al., Characterization of the 3xTg-AD mouse model of Alzheimer's disease: part 2. Behavioral and cognitive changes, Brain Res, vol. 12(1348):149-55, Aug. 2010 (ePub Jun. 2010).
GenBank: NP_000302; Web page https://www.ncbi.nlm.nih.gov/protein/NP_000302.1, 3 pages, retrieved from Internet on Aug. 4, 2020.
Office Action and Search Report dated Apr. 14, 2020 in the corresponding Russian Patent Application No. 2018119119 with unofficial English translation provided by the Agent.
Office Action issued in the counterpart Japanese Patent Application No. 2018-522093 dated Nov. 4, 2020 with an unofficial English translation provided by the Japanese Agent.
Communication pursuant to Article 94(3) EPC issued in the counterpart European Patent Application No. 16791770.7 dated Mar. 25, 2021.
Preliminary Office Action published in the counterpart Brazilian Patent Application No. BR112018008407-7 dated Mar. 23, 2021.
Van Seventer, J.M., and Hochberg, N.S., Principles of Infectious Diseases: Transmission, Diagnosis, Prevention, and Control, International Encyclopedia of Public Health, 2017, 6(2):22-39, epub, Oct. 24, 2016.
Levites, Y., et al., A Human Monoclonal IgG That Binds A-beta Assemblies and Diverse Amyloids Exhibits Anti-Amyloid Activities In Vitro and In Vivo, J. Neurosci., Apr. 22, 2015, 3 5(16):6265-6276.
Moutel, S., et al., A multi-Fc-species system for recombinant antibody production, BMC Biotechnology, Feb. 26, 2009, 9(14):1-9.
Second Office Action issued on Apr. 28, 2021 in the corresponding Russian Patent Application No. 2018119119 with unofficial English translation provided by the Agent.
Second Office Action issued on Apr. 14, 2021 in the counterpart Japanese Patent Application No. 2018-522093 with an unofficial English translation provided by the Agent.
Office Action issued on May 7, 2021 in the counterpart Chinese Patent Application No. 201680069956.4 with an unofficial English translation provided by the Agent.

\* cited by examiner

SEQUENCE LISTING

<160> NUMBER OF SEQ ID NOS: 15

<210> SEQ ID NO 1
<211> LENGTH: 6694
<212> TYPE: DNA
<213> ORGANISM: Artificial sequence
<220> FEATURE:
<223> OTHER INFORMATION: pAAV.CB7.CI.201IA.rBG
<220> FEATURE:
<221> NAME/KEY: polyA_signal
<222> LOCATION: (60)..(186)
<220> FEATURE:
<221> NAME/KEY: misc_feature
<222> LOCATION: (275)..(404)
<223> OTHER INFORMATION: 3' ITR (complement)
<220> FEATURE:
<221> NAME/KEY: rep_origin
<222> LOCATION: (581)..(1036)
<220> FEATURE:
<221> NAME/KEY: misc_feature
<222> LOCATION: (3226)..(3355)
<223> OTHER INFORMATION: 5' ITR
<220> FEATURE:
<221> NAME/KEY: misc
<222> LOCATION: (3423)..(3804)
<223> OTHER INFORMATION: CMV IE promoter
<220> FEATURE:
<221> NAME/KEY: promoter
<222> LOCATION: (3807)..(4088)
<220> FEATURE:
<221> NAME/KEY: TATA_signal
<222> LOCATION: (4061)..(4064)
<220> FEATURE:
<221> NAME/KEY: Intron
<222> LOCATION: (4183)..(5155)
<220> FEATURE:
<221> NAME/KEY: CDS
<222> LOCATION: (5161)..(6690)
<223> OTHER INFORMATION: 201IA

<400> SEQUENCE: 1

```
gtacctctag agtcgacccg gcggcctcg aggacggggt gaactacgcc tgaggatccg      60
atctttttcc ctctgccaaa aattatgggg acatcatgaa gccccttgag catctgactt    120
ctggctaata aaggaaattt attttcattg caatagtgtg ttggaatttt ttgtgtctct    180
cactcggaag caattcgttg atctgaattt cgaccaccca taatacccat taccctggta    240
gataagtagc atggcgggtt aatcattaac tacaaggaac ccctagtgat ggagttggcc    300
actccctctc tgcgcgctcg ctcgctcact gaggccgggc gaccaaaggt cgcccgacgc    360
ccgggctttg cccgggcggc ctcagtgagc gagcgagcgc gcagccttaa ttaacctaat    420
tcactggccg tcgttttaca acgtcgtgac tgggaaaacc ctggcgttac ccaacttaat    480
cgccttgcag cacatccccc tttcgccagc tggcgtaata gcgaagaggc ccgcaccgat    540
cgcccttccc aacagttgcg cagcctgaat ggcgaatggg acgcgccctg tagcggcgca    600
ttaagcgcgg cgggtgtggt ggttacgcgc agcgtgaccg ctacacttgc cagcgcccta    660
gcgcccgctc ctttcgcttt cttcccttcc tttctcgcca cgttcgccgg ctttccccgt    720
caagctctaa atcggggct ccctttaggg ttccgattta gtgctttacg gcacctcgac    780
cccaaaaaac ttgattaggg tgatggttca cgtagtgggc catcgccctg atagacggtt    840
tttcgccctt tgacgttgga gtccacgttc tttaatagtg gactcttgtt ccaaactgga    900
acaacactca accctatctc ggtctattct tttgatttat aagggatttt gccgatttcg    960
gcctattggt taaaaaatga gctgatttaa caaaaattta acgcgaattt taacaaaata   1020
ttaacgctta caatttaggt ggcacttttc ggggaaatgt gcgcggaacc cctatttgtt   1080
```

```
tatttttcta aatacattca aatatgtatc cgctcatgag acaataaccc tgataaatgc    1140
ttcaataata ttgaaaaagg aagagtatga gtattcaaca tttccgtgtc gcccttattc    1200
ccttttttgc ggcattttgc cttcctgttt ttgctcaccc agaaacgctg gtgaaagtaa    1260
aagatgctga agatcagttg ggtgcacgag tgggttacat cgaactggat ctcaacagcg    1320
gtaagatcct tgagagtttt cgccccgaag aacgttttcc aatgatgagc acttttaaag    1380
ttctgctatg tggcgcggta ttatcccgta ttgacgccgg gcaagagcaa ctcggtcgcc    1440
gcatacacta ttctcagaat gacttggttg agtactcacc agtcacagaa aagcatctta    1500
cggatggcat gacagtaaga gaattatgca gtgctgccat aaccatgagt gataacactg    1560
cggccaactt acttctgaca acgatcggag gaccgaagga gctaaccgct ttttttgcaca   1620 acatggggga tcatgtaact cgccttgatc gttgggaacc ggagctgaat gaagccatac    1680
caaacgacga gcgtgacacc acgatgcctg tagcaatggc aacaacgttg cgcaaactat    1740
taactggcga actacttact ctagcttccc ggcaacaatt aatagactgg atggaggcgg    1800
ataaagttgc aggaccactt ctgcgctcgg cccttccggc tggctggttt attgctgata    1860
aatctggagc cggtgagcgt gggtctcgcg gtatcattgc agcactgggg ccagatggta    1920
agccctcccg tatcgtagtt atctacacga cggggagtca ggcaactatg gatgaacgaa    1980
atagacagat cgctgagata ggtgcctcac tgattaagca ttggtaactg tcagaccaag    2040
tttactcata tatactttag attgatttaa aacttcattt ttaatttaaa aggatctagg    2100
tgaagatcct ttttgataat ctcatgacca aaatccctta acgtgagttt cgttccact    2160 gagcgtcaga ccccgtagaa aagatcaaag gatcttcttg agatcctttt tttctgcgcg    2220
taatctgctg cttgcaaaca aaaaaaccac cgctaccagc ggtggtttgt ttgccggatc    2280
aagagctacc aactctttt ccgaaggtaa ctggcttcag cagagcgcag ataccaaata    2340
ctgttcttct agtgtagccg tagttaggcc accacttcaa gaactctgta gcaccgccta    2400
catacctcgc tctgctaatc ctgttaccag tggctgctgc cagtggcgat aagtcgtgtc    2460
ttaccgggtt ggactcaaga cgatagttac cggataaggc gcagcggtcg ggctgaacgg    2520
ggggttcgtg cacacagccc agcttggagc gaacgaccta caccgaactg agatacctac    2580
agcgtgagct atgagaaagc gccacgcttc ccgaagggag aaaggcggac aggtatccgg    2640
taagcggcag ggtcggaaca ggagagcgca cgagggagct tccaggggga aacgcctggt    2700
atctttatag tcctgtcggg tttcgccacc tctgacttga gcgtcgattt ttgtgatgct    2760
cgtcaggggg gcggagccta tggaaaaacg ccagcaacgc ggcctttta cggttcctgg    2820 ccttttgctg gccttttgct cacatgttct ttcctgcgtt atcccctgat tctgtggata    2880
accgtattac cgcctttgag tgagctgata ccgctcgccg cagccgaacg accgagcgca    2940
gcgagtcagt gagcgaggaa gcggaagagc gcccaatacg caaaccgcct ctccccgcgc    3000
gttggccgat tcattaatgc agctggcacg acaggtttcc cgactggaaa gcgggcagtg    3060
agcgcaacgc aattaatgtg agttagctca ctcattaggc accccaggct ttacacttta    3120
tgcttccggc tcgtatgttg tgtggaattg tgagcggata acaatttcac acaggaaaca    3180
gctatgacca tgattacgcc agatttaatt aaggccttaa ttaggctgcg cgctcgctcg    3240
ctcactgagg ccgcccgggc aaagcccggg cgtcgggcga cctttggtcg cccggcctca    3300
gtgagcgagc gagcgcgcag agagggagtg gccaactcca tcactagggg ttccttgtag    3360
ttaatgatta cccgccatg ctacttatct accagggtaa tggggatcct ctagaactat    3420
agctagtcga cattgattat tgactagtta ttaatagtaa tcaattacgg ggtcattagt    3480
```

-continued

```
tcatagccca tatatggagt tccgcgttac ataacttacg gtaaatggcc cgcctggctg    3540
accgcccaac gaccccgcc cattgacgtc aataatgacg tatgttccca tagtaacgcc     3600
aatagggact ttccattgac gtcaatgggt ggactattta cggtaaactg cccacttggc    3660
agtacatcaa gtgtatcata tgccaagtac gccccctatt gacgtcaatg acggtaaatg    3720
gcccgcctgg cattatgccc agtacatgac cttatgggac tttcctactt ggcagtacat    3780
ctacgtatta gtcatcgcta ttaccatggt cgaggtgagc cccacgttct gcttcactct    3840
ccccatctcc ccccctccc caccccaat tttgtattta tttattttt aattattttg       3900
tgcagcgatg ggggcggggg ggggggggggg gcgcgcgcca ggcggggcgg ggcggggcga    3960
ggggcggggc ggggcgaggc ggagaggtgc ggcggcagcc aatcagagcg gcgcgctccg    4020
aaagtttcct tttatggcga ggcggcgcg gcggcggccc tataaaaagc gaagcgcgcg     4080
gcgggcgggg agtcgctgcg acgctgcctt cgccccgtgc cccgctccgc gccgcctcg    4140
cgccgcccgc cccggctctg actgaccgcg ttactcccac aggtgagcgg gcgggacggc    4200
ccttctcctc cgggctgtaa ttagcgcttg gtttaatgac ggcttgtttc ttttctgtgg    4260
ctgcgtgaaa gccttgaggg gctccggag gcccctttgt gcggggggag cggctcgggg    4320
ggtgcgtgcg tgtgtgtgtg cgtggggagc gccgcgtgcg gctccgcgct gcccggcggc    4380
tgtgagcgct gcgggcgcgg cgcggggctt tgtgcgctcc gcagtgtgcg cgaggggagc    4440
gcggccgggg gcggtgcccc gcggtgcggg gggggctgcg aggggaacaa aggctgcgtg    4500
cgggggtgtgt gcgtgggggg gtgagcaggg ggtgtgggcg cgtcggtcgg gctgcaaccc    4560
cccctgcacc ccctccccg agttgctgag cacggcccgg cttcgggtgc ggggctccgt    4620
acggggcgtg gcgcggggct cgccgtgccg ggcggggggt ggcggcaggt gggggtgccg    4680
ggcggggcgg ggccgcctcg ggccggggag ggctcggggg aggggcgcgg cggccccgg    4740
agcgccggcg gctgtcgagg gcggcgagc gcagccatt gccttttatg gtaatcgtgc    4800
gagagggcgc agggacttcc tttgtcccaa atctgtgcgg agccgaaatc tgggaggcgc    4860
cgccgcaccc cctctagcgg gcgcggggcg aagcggtgcg gcgccggcag gaaggaaatg   4920
ggcggggagg gccttcgtgc gtcgccgcgc cgccgtcccc ttctccctct ccagcctcgg    4980
ggctgtccgc gggggacgg ctgccttcgg ggggacggg gcagggcggg gttcggcttc     5040
tggcgtgtga ccgcggctc tagagcctct gctaaccatg ttcatgcctt cttctttttc    5100
ctacagctcc tgggcaacgt gctggttatt gtgctgtctc atcatttgg caaagaattc    5160
atg gag ttc ggg ctg agc tgg gtc ttt ctg gtg gcc ctg ctg aag gga    5208
Met Glu Phe Gly Leu Ser Trp Val Phe Leu Val Ala Leu Leu Lys Gly
1               5                   10                  15
gtc cag tgc gag gtg cag ctg ctg gaa tcc gga cct ggc ctg gtg aaa    5256
Val Gln Cys Glu Val Gln Leu Leu Glu Ser Gly Pro Gly Leu Val Lys
            20                  25                  30
cca tct gag aca ctg agt ctg act tgt gct gtc tcc ggc ctg tct atc    5304
Pro Ser Glu Thr Leu Ser Leu Thr Cys Ala Val Ser Gly Leu Ser Ile
        35                  40                  45
agc tcc gat ttc tcc tgg gca tgg att agg cag acc ccc ggc aag gcc    5352
Ser Ser Asp Phe Ser Trp Ala Trp Ile Arg Gln Thr Pro Gly Lys Ala
    50                  55                  60
ctg gaa tat gtg ggg tac atc cgc ggg aac acc gga gat aca tac tat    5400
Leu Glu Tyr Val Gly Tyr Ile Arg Gly Asn Thr Gly Asp Thr Tyr Tyr
65                  70                  75                  80
aat cct agt ctg aag tca agg ctg act atc tca aag gac acc agc aaa    5448
Asn Pro Ser Leu Lys Ser Arg Leu Thr Ile Ser Lys Asp Thr Ser Lys
```

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |
| aac | caa | atc | tac | ctg | aat | ctg | tct | agt | gtc | acc | gct | ggc | gat | gcc | gcc |
| Asn | Gln | Ile | Tyr | Leu | Asn | Leu | Ser | Ser | Val | Thr | Ala | Gly | Asp | Ala | Ala |
|  |  |  | 100 |  |  |  |  | 105 |  |  |  |  | 110 |  |  |
| gtg | tac | tat | tgc | gca | agg | gac | cgg | gtg | tgc | gac | gat | gac | tac | gga | tac |
| Val | Tyr | Tyr | Cys | Ala | Arg | Asp | Arg | Val | Cys | Asp | Asp | Asp | Tyr | Gly | Tyr |
|  |  | 115 |  |  |  |  | 120 |  |  |  |  | 125 |  |  |  |
| tat | tac | acc | gag | gtg | tgc | ttc | ggc | ctg | gat | tct | tgg | ggg | cag | gga | atc |
| Tyr | Tyr | Thr | Glu | Val | Cys | Phe | Gly | Leu | Asp | Ser | Trp | Gly | Gln | Gly | Ile |
| 130 |  |  |  |  | 135 |  |  |  |  | 140 |  |  |  |  |  |
| gtg | gtc | aca | gtg | tca | agc | ggc | gga | ggc | agc | gga | gga | ggg | tcc |  |  |
| Val | Val | Thr | Val | Ser | Ser | Gly | Gly | Gly | Ser | Gly | Gly | Gly | Ser |  |  |
| 145 |  |  |  | 150 |  |  |  |  | 155 |  |  |  | 160 |  |  |
| gga | ggc | ggg | gga | tct | gca | gaa | ctg | gtc | atg | aca | cag | tcc | cca | ctg | agc |
| Gly | Gly | Gly | Gly | Ser | Ala | Glu | Leu | Val | Met | Thr | Gln | Ser | Pro | Leu | Ser |
|  |  |  |  | 165 |  |  |  |  | 170 |  |  |  |  | 175 |  |
| ctg | tcc | gtc | gct | cca | gga | cag | act | gca | tct | att | agt | tgt | cga | tcc | tct |
| Leu | Ser | Val | Ala | Pro | Gly | Gln | Thr | Ala | Ser | Ile | Ser | Cys | Arg | Ser | Ser |
|  |  |  | 180 |  |  |  |  | 185 |  |  |  |  | 190 |  |  |
| cag | tcc | ctg | gac | tat | gct | aac | ggc | aat | acc | tac | ctg | tct | tgg | ttt | cac |
| Gln | Ser | Leu | Asp | Tyr | Ala | Asn | Gly | Asn | Thr | Tyr | Leu | Ser | Trp | Phe | His |
|  |  | 195 |  |  |  |  | 200 |  |  |  |  | 205 |  |  |  |
| cag | cga | cca | gga | cag | cca | cct | cgg | aga | ctg | atc | tat | cag | att | tcc | aac |
| Gln | Arg | Pro | Gly | Gln | Pro | Pro | Arg | Arg | Leu | Ile | Tyr | Gln | Ile | Ser | Asn |
| 210 |  |  |  |  | 215 |  |  |  |  | 220 |  |  |  |  |  |
| aga | gat | tct | gga | gtg | ccc | gac | agg | ttc | tca | ggc | agc | gga | gca | gga | act |
| Arg | Asp | Ser | Gly | Val | Pro | Asp | Arg | Phe | Ser | Gly | Ser | Gly | Ala | Gly | Thr |
| 225 |  |  |  | 230 |  |  |  |  | 235 |  |  |  |  | 240 |  |
| gag | ttt | acc | ctg | cga | atc | agt | cgg | atg | gaa | tca | gat | gac | gtg | ggg | atc |
| Glu | Phe | Thr | Leu | Arg | Ile | Ser | Arg | Met | Glu | Ser | Asp | Asp | Val | Gly | Ile |
|  |  |  |  | 245 |  |  |  |  | 250 |  |  |  |  | 255 |  |
| tac | tac | tgc | gga | cag | ggg | acc | aca | ttc | cca | cgg | aca | ttt | gga | cag | ggc |
| Tyr | Tyr | Cys | Gly | Gln | Gly | Thr | Thr | Phe | Pro | Arg | Thr | Phe | Gly | Gln | Gly |
|  |  |  | 260 |  |  |  |  | 265 |  |  |  |  | 270 |  |  |
| act | aag | gtg | gag | atc | aaa | acc | tgt | gga | gga | gga | agc | aag | cca | cca | acc |
| Thr | Lys | Val | Glu | Ile | Lys | Thr | Cys | Gly | Gly | Gly | Ser | Lys | Pro | Pro | Thr |
|  |  | 275 |  |  |  |  | 280 |  |  |  |  | 285 |  |  |  |
| tgc | cct | cca | tgt | aca | tct | ccc | gaa | ctg | ctg | ggc | ggg | cct | agc | gtg | ttc |
| Cys | Pro | Pro | Cys | Thr | Ser | Pro | Glu | Leu | Leu | Gly | Gly | Pro | Ser | Val | Phe |
|  | 290 |  |  |  |  | 295 |  |  |  |  | 300 |  |  |  |  |
| ctg | ttt | ccc | cct | aag | cct | aaa | gat | aca | ctg | atg | att | agt | aga | acc | cca |
| Leu | Phe | Pro | Pro | Lys | Pro | Lys | Asp | Thr | Leu | Met | Ile | Ser | Arg | Thr | Pro |
| 305 |  |  |  |  | 310 |  |  |  |  | 315 |  |  |  |  | 320 |
| gag | gtc | aca | tgc | gtg | gtc | gtg | gac | gtg | tcc | cag | gaa | gat | cct | gac | gtg |
| Glu | Val | Thr | Cys | Val | Val | Val | Asp | Val | Ser | Gln | Glu | Asp | Pro | Asp | Val |
|  |  |  | 325 |  |  |  |  | 330 |  |  |  |  | 335 |  |  |
| aag | ttc | aac | tgg | tac | gtg | aat | ggc | gcc | gag | gtg | cac | cat | gct | cag | act |
| Lys | Phe | Asn | Trp | Tyr | Val | Asn | Gly | Ala | Glu | Val | His | His | Ala | Gln | Thr |
|  |  |  | 340 |  |  |  |  | 345 |  |  |  |  | 350 |  |  |
| aaa | cca | cgc | gaa | acc | cag | tat | aat | agt | aca | tac | cga | gtc | gtg | tca | gtc |
| Lys | Pro | Arg | Glu | Thr | Gln | Tyr | Asn | Ser | Thr | Tyr | Arg | Val | Val | Ser | Val |
|  | 355 |  |  |  |  | 360 |  |  |  |  | 365 |  |  |  |  |
| ctg | aca | gtg | act | cac | cag | gat | tgg | ctg | aac | ggc | aag | gag | tat | acc | tgc |
| Leu | Thr | Val | Thr | His | Gln | Asp | Trp | Leu | Asn | Gly | Lys | Glu | Tyr | Thr | Cys |
| 370 |  |  |  |  | 375 |  |  |  |  | 380 |  |  |  |  |  |
| aag | gtg | tct | aac | aag | gcc | ctg | ccc | gcc | cct | atc | cag | aaa | aca | att | agc |
| Lys | Val | Ser | Asn | Lys | Ala | Leu | Pro | Ala | Pro | Ile | Gln | Lys | Thr | Ile | Ser |
| 385 |  |  |  |  | 390 |  |  |  |  | 395 |  |  |  |  | 400 |
| aag | gac | aaa | ggg | cag | cca | cgg | gaa | ccc | cag | gtg | tac | act | ctg | cca | ccc |

5496

5544

5592

5640

5688

5736

5784

5832

5880

5928

5976

6024

6072

6120

6168

6216

6264

6312

6360

6408

```
Lys Asp Lys Gly Gln Pro Arg Glu Pro Gln Val Tyr Thr Leu Pro Pro
                405                 410                 415 tca aga gag gaa ctg act aag aac cag gtc agc ctg acc tgt ctg gtg      6456
Ser Arg Glu Glu Leu Thr Lys Asn Gln Val Ser Leu Thr Cys Leu Val
            420                 425                 430 aaa ggc ttc tac ccc agc gat atc gtc gtg gag tgg gaa agt tca ggc      6504
Lys Gly Phe Tyr Pro Ser Asp Ile Val Val Glu Trp Glu Ser Ser Gly
                435                 440                 445 cag cct gag aat act tac aag act acc cct cca gtg ctg gat agc gac      6552
Gln Pro Glu Asn Thr Tyr Lys Thr Thr Pro Pro Val Leu Asp Ser Asp
        450                 455                 460 ggg tcc tat ttc ctg tac agc aag ctg aca gtg gac aaa tcc cgc tgg      6600
Gly Ser Tyr Phe Leu Tyr Ser Lys Leu Thr Val Asp Lys Ser Arg Trp
465                 470                 475                 480 cag cag gga aac gtc ttt tcc tgt tct gtg atg cat gag gcc ctg cac      6648
Gln Gln Gly Asn Val Phe Ser Cys Ser Val Met His Glu Ala Leu His
                485                 490                 495 aat cat tac acc cag aag agt ctg tca ctg agc ccc ggc aaa tgag         6694
Asn His Tyr Thr Gln Lys Ser Leu Ser Leu Ser Pro Gly Lys
                500                 505                 510

<210> SEQ ID NO 2
<211> LENGTH: 510
<212> TYPE: PRT
<213> ORGANISM: Artificial sequence
<220> FEATURE:
<223> OTHER INFORMATION: Synthetic Construct

<400> SEQUENCE: 2

Met Glu Phe Gly Leu Ser Trp Val Phe Leu Val Ala Leu Leu Lys Gly
1               5                   10                  15

Val Gln Cys Glu Val Gln Leu Leu Glu Ser Gly Pro Gly Leu Val Lys
            20                  25                  30

Pro Ser Glu Thr Leu Ser Leu Thr Cys Ala Val Ser Gly Leu Ser Ile
        35                  40                  45

Ser Ser Asp Phe Ser Trp Ala Trp Ile Arg Gln Thr Pro Gly Lys Ala
    50                  55                  60

Leu Glu Tyr Val Gly Tyr Ile Arg Gly Asn Thr Gly Asp Thr Tyr Tyr
65                  70                  75                  80

Asn Pro Ser Leu Lys Ser Arg Leu Thr Ile Ser Lys Asp Thr Ser Lys
                85                  90                  95

Asn Gln Ile Tyr Leu Asn Leu Ser Ser Val Thr Ala Gly Asp Ala Ala
            100                 105                 110

Val Tyr Tyr Cys Ala Arg Asp Arg Val Cys Asp Asp Tyr Gly Tyr
        115                 120                 125

Tyr Tyr Thr Glu Val Cys Phe Gly Leu Asp Ser Trp Gly Gln Gly Ile
    130                 135                 140

Val Val Thr Val Ser Ser Gly Gly Gly Ser Gly Gly Gly Ser
145                 150                 155                 160

Gly Gly Gly Gly Ser Ala Glu Leu Val Met Thr Gln Ser Pro Leu Ser
                165                 170                 175

Leu Ser Val Ala Pro Gly Gln Thr Ala Ser Ile Ser Cys Arg Ser Ser
            180                 185                 190

Gln Ser Leu Asp Tyr Ala Asn Gly Asn Thr Tyr Leu Ser Trp Phe His
        195                 200                 205

Gln Arg Pro Gly Gln Pro Pro Arg Arg Leu Ile Tyr Gln Ile Ser Asn
    210                 215                 220
```

```
Arg Asp Ser Gly Val Pro Asp Arg Phe Ser Gly Ser Gly Ala Gly Thr
225                 230                 235                 240

Glu Phe Thr Leu Arg Ile Ser Arg Met Glu Ser Asp Asp Val Gly Ile
                245                 250                 255

Tyr Tyr Cys Gly Gln Gly Thr Thr Phe Pro Arg Thr Phe Gly Gln Gly
            260                 265                 270

Thr Lys Val Glu Ile Lys Thr Cys Gly Gly Gly Ser Lys Pro Pro Thr
        275                 280                 285

Cys Pro Pro Cys Thr Ser Pro Glu Leu Leu Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser Gln Glu Asp Pro Asp Val
                325                 330                 335

Lys Phe Asn Trp Tyr Val Asn Gly Ala Glu Val His His Ala Gln Thr
            340                 345                 350

Lys Pro Arg Glu Thr Gln Tyr Asn Ser Thr Tyr Arg Val Val Ser Val
        355                 360                 365

Leu Thr Val Thr His Gln Asp Trp Leu Asn Gly Lys Glu Tyr Thr Cys
370                 375                 380

Lys Val Ser Asn Lys Ala Leu Pro Ala Pro Ile Gln Lys Thr Ile Ser
385                 390                 395                 400

Lys Asp Lys Gly Gln Pro Arg Glu Pro Gln Val Tyr Thr Leu Pro Pro
                405                 410                 415

Ser Arg Glu Glu Leu Thr Lys Asn Gln Val Ser Leu Thr Cys Leu Val
            420                 425                 430

Lys Gly Phe Tyr Pro Ser Asp Ile Val Val Glu Trp Glu Ser Ser Gly
        435                 440                 445

Gln Pro Glu Asn Thr Tyr Lys Thr Thr Pro Pro Val Leu Asp Ser Asp
    450                 455                 460

Gly Ser Tyr Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510

<210> SEQ ID NO 3
<211> LENGTH: 6694
<212> TYPE: DNA
<213> ORGANISM: Artificial sequence
<220> FEATURE:
<223> OTHER INFORMATION: Plasmid encoding 201IA(I253A)mutant
<220> FEATURE:
<221> NAME/KEY: misc
<222> LOCATION: (1)..(130)
<223> OTHER INFORMATION: 5' ITR
<220> FEATURE:
<221> NAME/KEY: misc_feature
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (958)..(1930)
```

```
<223> OTHER INFORMATION: chicken beta-actin intron
<220> FEATURE:
<221> NAME/KEY: CDS
<222> LOCATION: (1936)..(3465)
<223> OTHER INFORMATION: CMV IE promoter
<220> FEATURE:
<221> NAME/KEY: polyA_signal
<222> LOCATION: (3529)..(3655)
<223> OTHER INFORMATION: rabbit globin polyA
<220> FEATURE:
<221> NAME/KEY: misc_feature
<222> LOCATION: (3744)..(3873)
<223> OTHER INFORMATION: 3' ITR (complement)
<220> FEATURE:
<221> NAME/KEY: rep_origin
<222> LOCATION: (4050)..(4505)
<220> FEATURE:
<221> NAME/KEY: misc_feature
<222> LOCATION: (4636)..(5493)
<223> OTHER INFORMATION: AP(R) marker
<220> FEATURE:
<221> NAME/KEY: rep_origin
<222> LOCATION: (5667)..(6255)

<400> SEQUENCE: 3
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggact atttacggta     420
aactgcccac ttggcagtac atcaagtgta tcatatgcca gtacgccccc tattgacgt      480 caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccccc ctccccaccc ccaattttgt atttatttat     660
tttttaatta ttttgtgcag cgatgggggc ggggggggg gggggcgcg cgccaggcgg     720 ggcggggcgg ggcgaggggc ggggcgggc gaggcggaga ggtgcggcgg cagccaatca     780
gagcggcgcg ctccgaaagt tcctttttat ggcgaggcgg cggcggcggc ggccctataa     840
aaagcgaagc gcgcggcggg cggggagtcg ctgcgacgct gccttcgccc cgtgccccgc     900
tccgccgccg cctcgcgccg cccgccccgg ctctgactga ccgcgttact cccacaggtg     960
agcgggcggg acggcccttc tcctccgggc tgtaattagc gcttggttta atgacggctt    1020
gtttcttttc tgtggctgcg tgaaagcctt gaggggctcc ggggagggcc tttgtgcggg    1080
gggagcggct cgggggtgc gtgcgtgtgt gtgtgcgtgg ggagcgccgc gtgcggctcc    1140
gcgctgcccg gcggctgtga gcgctgcggg cgcggcgcgg ggctttgtgc gctccgcagt    1200
gtgcgcgagg ggagcgcggc cggggcggt gccccgcgt gcggggggg ctgcgagggg     1260 aacaaaggct gcgtgcgggg tgtgtgcgtg ggggggtgag caggggtgt gggcgcgtcg    1320 gtcgggctgc aacccccccct gcacccccct ccccagagttg ctgagcacgg cccggcttcg    1380 ggtgcgggc tccgtacggg gcgtggcgcg gggctcgccg tgccgggcgg ggggtggcgg    1440
caggtggggg tgccgggcgg ggcggggccg cctcgggccg gggagggctc ggggagggg    1500 cgcggcggcc cccggagcgc cggcggctgt cgaggcgcgg cgagccgcag ccattgcctt    1560
ttatggtaat cgtgcgagag ggcgcaggga cttcctttgt cccaaatctg tgcggagccg    1620
```

```
                                                        -continued aaatctggga ggcgccgccg caccccctct agcgggcgcg gggcgaagcg gtgcggcgcc     1680
ggcaggaagg aaatgggcgg ggagggcctt cgtgcgtcgc cgcgccgccg tccccttctc     1740
cctctccagc ctcggggctg tccgcggggg gacggctgcc ttcgggggg acggggcagg      1800 gcggggttcg gcttctggcg tgtgaccggc ggctctagag cctctgctaa ccatgttcat     1860
gccttcttct ttttcctaca gctcctgggc aacgtgctgg ttattgtgct gtctcatcat    1920
tttggcaaag aattc atg gag ttc ggg ctg agc tgg gtc ttt ctg gtg gcc    1971
              Met Glu Phe Gly Leu Ser Trp Val Phe Leu Val Ala
                1               5                  10 ctg ctg aag gga gtc cag tgc gag gtg cag ctg ctg gaa tcc gga cct      2019
Leu Leu Lys Gly Val Gln Cys Glu Val Gln Leu Leu Glu Ser Gly Pro
         15                  20                  25 ggc ctg gtg aaa cca tct gag aca ctg agt ctg act tgt gct gtc tcc      2067
Gly Leu Val Lys Pro Ser Glu Thr Leu Ser Leu Thr Cys Ala Val Ser
 30                  35                  40 ggc ctg tct atc agc tcc gat ttc tcc tgg gca tgg att agg cag acc      2115
Gly Leu Ser Ile Ser Ser Asp Phe Ser Trp Ala Trp Ile Arg Gln Thr
45                  50                  55                  60 ccc ggc aag gcc ctg gaa tat gtg ggg tac atc cgc ggg aac acc gga      2163
Pro Gly Lys Ala Leu Glu Tyr Val Gly Tyr Ile Arg Gly Asn Thr Gly
                 65                  70                  75 gat aca tac tat aat cct agt ctg aag tca agg ctg act atc tca aag      2211
Asp Thr Tyr Tyr Asn Pro Ser Leu Lys Ser Arg Leu Thr Ile Ser Lys
             80                  85                  90 gac acc agc aaa aac caa atc tac ctg aat ctg tct agt gtc acc gct      2259
Asp Thr Ser Lys Asn Gln Ile Tyr Leu Asn Leu Ser Ser Val Thr Ala
         95                 100                 105 ggc gat gcc gcc gtg tac tat tgc gca agg gac cgg gtg tgc gac gat      2307
Gly Asp Ala Ala Val Tyr Tyr Cys Ala Arg Asp Arg Val Cys Asp Asp
    110                 115                 120 gac tac gga tac tat tac acc gag gtg tgc ttc ggc ctg gat tct tgg      2355
Asp Tyr Gly Tyr Tyr Tyr Thr Glu Val Cys Phe Gly Leu Asp Ser Trp
125                 130                 135                 140 ggg cag gga atc gtg gtc aca gtg tca agc ggc gga gga ggc agc gga      2403
Gly Gln Gly Ile Val Val Thr Val Ser Ser Gly Gly Gly Gly Ser Gly
                145                 150                 155 gga gga ggg tcc gga ggc ggg gga tct gca gaa ctg gtc atg aca cag      2451
Gly Gly Gly Ser Gly Gly Gly Gly Ser Ala Glu Leu Val Met Thr Gln
            160                 165                 170 tcc cca ctg agc ctg tcc gtc gct cca gga cag act gca tct att agt      2499
Ser Pro Leu Ser Leu Ser Val Ala Pro Gly Gln Thr Ala Ser Ile Ser
        175                 180                 185 tgt cga tcc tct cag tcc ctg gac tat gct aac ggc aat acc tac ctg      2547
Cys Arg Ser Ser Gln Ser Leu Asp Tyr Ala Asn Gly Asn Thr Tyr Leu
    190                 195                 200 tct tgg ttt cac cag cga cca gga cag cca cct cgg aga ctg atc tat      2595
Ser Trp Phe His Gln Arg Pro Gly Gln Pro Pro Arg Arg Leu Ile Tyr
205                 210                 215                 220 cag att tcc aac aga gat tct gga gtg ccc gac agg ttc tca ggc agc      2643
Gln Ile Ser Asn Arg Asp Ser Gly Val Pro Asp Arg Phe Ser Gly Ser
                225                 230                 235 gga gca gga act gag ttt acc ctg cga atc agt cgg atg gaa tca gat      2691
Gly Ala Gly Thr Glu Phe Thr Leu Arg Ile Ser Arg Met Glu Ser Asp
            240                 245                 250 gac gtg ggg atc tac tac tgc gga cag ggg acc aca ttc cca cgg aca      2739
Asp Val Gly Ile Tyr Tyr Cys Gly Gln Gly Thr Thr Phe Pro Arg Thr
        255                 260                 265
```

-continued

| | |
|---|---|
| ttt gga cag ggc act aag gtg gag atc aaa acc tgt gga gga gga agc<br>Phe Gly Gln Gly Thr Lys Val Glu Ile Lys Thr Cys Gly Gly Gly Ser<br>270                      275                      280 | 2787 |
| aag cca cca acc tgc cct cca tgt aca tct ccc gaa ctg ctg ggc ggg<br>Lys Pro Pro Thr Cys Pro Pro Cys Thr Ser Pro Glu Leu Leu Gly Gly<br>285                      290                    295                  300 | 2835 |
| cct agc gtg ttc ctg ttt ccc cct aag cct aaa gat aca ctg atg gcc<br>Pro Ser Val Phe Leu Phe Pro Pro Lys Pro Lys Asp Thr Leu Met Ala<br>                   305                    310                    315 | 2883 |
| agt aga acc cca gag gtc aca tgc gtg gtg gtg gac gtg tcc cag gaa<br>Ser Arg Thr Pro Glu Val Thr Cys Val Val Val Asp Val Ser Gln Glu<br>                  320                  325                    330 | 2931 |
| gat cct gac gtg aag ttc aac tgg tac gtg aat ggc gcc gag gtg cac<br>Asp Pro Asp Val Lys Phe Asn Trp Tyr Val Asn Gly Ala Glu Val His<br>335                      340                    345 | 2979 |
| cat gct cag act aaa cca cgc gaa acc cag tat aat agt aca tac cga<br>His Ala Gln Thr Lys Pro Arg Glu Thr Gln Tyr Asn Ser Thr Tyr Arg<br>    350                    355                    360 | 3027 |
| gtc gtg tca gtc ctg aca gtg act cac cag gat tgg ctg aac ggc aag<br>Val Val Ser Val Leu Thr Val Thr His Gln Asp Trp Leu Asn Gly Lys<br>365                      370                    375                  380 | 3075 |
| gag tat acc tgc aag gtg tct aac aag gcc ctg ccc gcc cct atc cag<br>Glu Tyr Thr Cys Lys Val Ser Asn Lys Ala Leu Pro Ala Pro Ile Gln<br>                  385                  390                    395 | 3123 |
| aaa aca att agc aag gac aaa ggg cag cca cgg gaa ccc cag gtg tac<br>Lys Thr Ile Ser Lys Asp Lys Gly Gln Pro Arg Glu Pro Gln Val Tyr<br>                    400                    405                    410 | 3171 |
| act ctg cca ccc tca aga gag gaa ctg act aag aac cag gtc agc ctg<br>Thr Leu Pro Pro Ser Arg Glu Glu Leu Thr Lys Asn Gln Val Ser Leu<br>415                      420                    425 | 3219 |
| acc tgt ctg gtg aaa ggc ttc tac ccc agc gat atc gtc gtg gag tgg<br>Thr Cys Leu Val Lys Gly Phe Tyr Pro Ser Asp Ile Val Val Glu Trp<br>    430                    435                    440 | 3267 |
| gaa agt tca ggc cag cct gag aat act tac aag act acc cct cca gtg<br>Glu Ser Ser Gly Gln Pro Glu Asn Thr Tyr Lys Thr Thr Pro Pro Val<br>445                      450                    455                  460 | 3315 |
| ctg gat agc gac ggg tcc tat ttc ctg tac agc aag ctg aca gtg gac<br>Leu Asp Ser Asp Gly Ser Tyr Phe Leu Tyr Ser Lys Leu Thr Val Asp<br>                  465                  470                    475 | 3363 |
| aaa tcc cgc tgg cag cag gga aac gtc ttt tcc tgt tct gtg atg cat<br>Lys Ser Arg Trp Gln Gln Gly Asn Val Phe Ser Cys Ser Val Met His<br>                    480                    485                    490 | 3411 |
| gag gcc ctg cac aat cat tac acc cag aag agt ctg tca ctg agc ccc<br>Glu Ala Leu His Asn His Tyr Thr Gln Lys Ser Leu Ser Leu Ser Pro<br>495                      500                    505 | 3459 |
| ggc aaa tgaggtacct ctagagtcga cccgggcggc ctcgaggacg gggtgaacta<br>Gly Lys<br>    510 | 3515 |
| cgcctgagga tccgatcttt ttccctctgc caaaaattat ggggacatca tgaagcccct | 3575 |
| tgagcatctg acttctggct aataaaggaa atttattttc attgcaatag tgtgttggaa | 3635 |
| ttttttgtgt ctctcactcg gaagcaattc gttgatctga atttcgacca cccataatac | 3695 |
| ccattaccct ggtagataag tagcatggcg ggttaatcat taactacaag gaacccctag | 3755 |
| tgatggagtt ggccactccc tctctgcgcg ctcgctcgct cactgaggcc gggcgaccaa | 3815 |
| aggtcgcccg acgcccgggc tttgcccggg cggcctcagt gagcgagcga gcgcgcagcc | 3875 |
| ttaattaacc taattcactg gccgtcgttt tacaacgtcg tgactgggaa accctggcg | 3935 |
| ttacccaact taatcgcctt gcagcacatc cccctttcgc cagctggcgt aatagcgaag | 3995 |

```
aggcccgcac cgatcgccct tcccaacagt tgcgcagcct gaatggcgaa tgggacgcgc    4055
cctgtagcgg cgcattaagc gcggcgggtg tggtggttac gcgcagcgtg accgctacac    4115
ttgccagcgc cctagcgccc gctcctttcg ctttcttccc ttcctttctc gccacgttcg    4175
ccggctttcc ccgtcaagct ctaaatcggg gctcccttt agggttccga tttagtgctt     4235
tacggcacct cgaccccaaa aaacttgatt agggtgatgg ttcacgtagt gggccatcgc    4295
cctgatagac ggttttttcgc cctttgacgt tggagtccac gttctttaat agtggactct   4355
tgttccaaac tggaacaaca ctcaaccta tctcggtcta ttcttttgat ttataaggga     4415
ttttgccgat ttcggcctat tggttaaaaa atgagctgat ttaacaaaaa tttaacgcga    4475
atttaacaa atattaacg cttacaattt aggtggcact tttcggggaa atgtgcgcgg      4535
aacccctatt tgtttatttt tctaaataca ttcaaatatg tatccgctca tgagacaata    4595
accctgataa atgcttcaat aatattgaaa aggaagagt atgagtattc aacatttccg     4655
tgtcgccctt attcccttt ttgcggcatt ttgccttcct gttttgctc acccagaaac      4715
gctggtgaaa gtaaaagatg ctgaagatca gttgggtgca cgagtgggtt acatcgaact    4775
ggatctcaac agcggtaaga tccttgagag ttttcgcccc gaagaacgtt ttccaatgat    4835
gagcactttt aaagttctgc tatgtggcgc ggtattatcc cgtattgacg ccgggcaaga   4895
gcaactcggt cgccgcatac actattctca gaatgacttg gttgagtact caccagtcac    4955
agaaaagcat cttacggatg gcatgacagt aagagaatta tgcagtgctg ccataaccat    5015
gagtgataac actgcggcca acttacttct gacaacgatc ggaggaccga aggagctaac    5075
cgcttttttg cacaacatgg gggatcatgt aactcgcctt gatcgttggg aaccggagct    5135
gaatgaagcc ataccaaacg acgagcgtga ccaccacgatg cctgtagcaa tggcaacaac   5195
gttgcgcaaa ctattaactg gcgaactact tactctagct tcccggcaac aattaataga    5255
ctggatggag gcggataaag ttgcaggacc acttctgcgc tcggcccttc cggctggctg    5315
gtttattgct gataaatctg gagccggtga gcgtgggtct cgcggtatca ttgcagcact    5375
ggggccagat ggtaagccct cccgtatcgt agttatctac acgacgggga gtcaggcaac    5435
tatgatgaa cgaaatagac agatcgctga gataggtgcc tcactgatta agcattggta     5495
actgtcagac caagtttact catatatact ttagattgat ttaaaacttc atttttaatt    5555
taaaaggatc taggtgaaga tccttttga taatctcatg accaaaatcc cttaacgtga    5615
gttttcgttc cactgagcgt cagacccccgt agaaaagatc aaaggatctt cttgagatcc   5675
tttttttctg cgcgtaatct gctgcttgca acaaaaaaa ccaccgctac cagcggtggt    5735
ttgtttgccg gatcaagagc taccaactct ttttccgaag gtaactggct tcagcagagc    5795
gcagatacca aatactgttc ttctagtgta gccgtagtta ggccaccact tcaagaactc    5855
tgtagcaccg cctacatacc tcgctctgct aatcctgtta ccagtggctg ctgccagtgg    5915
cgataagtcg tgtcttaccg ggttggactc aagacgatag ttaccggata aggcgcagcg    5975
gtcgggctga acggggggtt cgtgcacaca gcccagcttg gagcgaacga cctacaccga    6035
actgagatac ctacagcgtg agctatgaga aagcgccacg cttcccgaag ggagaaaggc    6095
ggacaggtat ccggtaagcg gcagggtcgg aacaggagag cgcacgaggg agcttccagg    6155
gggaaacgcc tggtatcttt atagtcctgt cgggtttcgc cacctctgac ttgagcgtcg    6215
atttttgtga tgctcgtcag gggggcggag cctatggaaa aacgccagca acgcggcctt    6275
tttacggttc ctggccttt gctggccttt tgctcacatg ttctttcctg cgttatcccc      6335
```

-continued

```
tgattctgtg gataaccgta ttaccgcctt tgagtgagct gataccgctc gccgcagccg      6395
aacgaccgag cgcagcgagt cagtgagcga ggaagcggaa gagcgcccaa tacgcaaacc      6455
gcctctcccc gcgcgttggc cgattcatta atgcagctgg cacgacaggt ttcccgactg      6515
gaaagcgggc agtgagcgca acgcaattaa tgtgagttag ctcactcatt aggcaccccca    6575 ggctttacac tttatgcttc cggctcgtat gttgtgtgga attgtgagcg gataacaatt     6635
tcacacagga aacagctatg accatgatta cgccagattt aattaaggcc ttaattagg      6694
```

<210> SEQ ID NO 4
<211> LENGTH: 510
<212> TYPE: PRT
<213> ORGANISM: Artificial sequence
<220> FEATURE:
<223> OTHER INFORMATION: Synthetic Construct

<400> SEQUENCE: 4

```
Met Glu Phe Gly Leu Ser Trp Val Phe Leu Val Ala Leu Leu Lys Gly
1               5                   10                  15

Val Gln Cys Glu Val Gln Leu Leu Glu Ser Gly Pro Gly Leu Val Lys
            20                  25                  30

Pro Ser Glu Thr Leu Ser Leu Thr Cys Ala Val Ser Gly Leu Ser Ile
        35                  40                  45

Ser Ser Asp Phe Ser Trp Ala Trp Ile Arg Gln Thr Pro Gly Lys Ala
    50                  55                  60

Leu Glu Tyr Val Gly Tyr Ile Arg Gly Asn Thr Gly Asp Thr Tyr Tyr
65                  70                  75                  80

Asn Pro Ser Leu Lys Ser Arg Leu Thr Ile Ser Lys Asp Thr Ser Lys
                85                  90                  95

Asn Gln Ile Tyr Leu Asn Leu Ser Ser Val Thr Ala Gly Asp Ala Ala
            100                 105                 110

Val Tyr Tyr Cys Ala Arg Asp Arg Val Cys Asp Asp Tyr Gly Tyr
        115                 120                 125

Tyr Tyr Thr Glu Val Cys Phe Gly Leu Asp Ser Trp Gly Gln Gly Ile
    130                 135                 140

Val Val Thr Val Ser Ser Gly Gly Gly Ser Gly Gly Gly Gly Ser
145                 150                 155                 160

Gly Gly Gly Gly Ser Ala Glu Leu Val Met Thr Gln Ser Pro Leu Ser
                165                 170                 175

Leu Ser Val Ala Pro Gly Gln Thr Ala Ser Ile Ser Cys Arg Ser Ser
            180                 185                 190

Gln Ser Leu Asp Tyr Ala Asn Gly Asn Thr Tyr Leu Ser Trp Phe His
        195                 200                 205

Gln Arg Pro Gly Gln Pro Pro Arg Arg Leu Ile Tyr Gln Ile Ser Asn
    210                 215                 220

Arg Asp Ser Gly Val Pro Asp Arg Phe Ser Gly Ser Gly Ala Gly Thr
225                 230                 235                 240

Glu Phe Thr Leu Arg Ile Ser Arg Met Glu Ser Asp Asp Val Gly Ile
                245                 250                 255

Tyr Tyr Cys Gly Gln Gly Thr Thr Phe Pro Arg Thr Phe Gly Gln Gly
            260                 265                 270

Thr Lys Val Glu Ile Lys Thr Cys Gly Gly Gly Ser Lys Pro Pro Thr
        275                 280                 285

Cys Pro Pro Cys Thr Ser Pro Glu Leu Leu Gly Gly Pro Ser Val Phe
    290                 295                 300
```

```
Leu Phe Pro Pro Lys Pro Lys Asp Thr Leu Met Ala Ser Arg Thr Pro
305                 310                 315                 320

Glu Val Thr Cys Val Val Val Asp Val Ser Gln Glu Asp Pro Asp Val
            325                 330                 335

Lys Phe Asn Trp Tyr Val Asn Gly Ala Glu Val His His Ala Gln Thr
        340                 345                 350

Lys Pro Arg Glu Thr Gln Tyr Asn Ser Thr Tyr Arg Val Val Ser Val
    355                 360                 365

Leu Thr Val Thr His Gln Asp Trp Leu Asn Gly Lys Glu Tyr Thr Cys
370                 375                 380

Lys Val Ser Asn Lys Ala Leu Pro Ala Pro Ile Gln Lys Thr Ile Ser
385                 390                 395                 400

Lys Asp Lys Gly Gln Pro Arg Glu Pro Gln Val Tyr Thr Leu Pro Pro
            405                 410                 415

Ser Arg Glu Glu Leu Thr Lys Asn Gln Val Ser Leu Thr Cys Leu Val
        420                 425                 430

Lys Gly Phe Tyr Pro Ser Asp Ile Val Val Glu Trp Glu Ser Ser Gly
    435                 440                 445

Gln Pro Glu Asn Thr Tyr Lys Thr Thr Pro Pro Val Leu Asp Ser Asp
450                 455                 460

Gly Ser Tyr Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
            485                 490                 495

Asn His Tyr Thr Gln Lys Ser Leu Ser Leu Ser Pro Gly Lys
        500                 505                 510

<210> SEQ ID NO 5
<211> LENGTH: 6694
<212> TYPE: DNA
<213> ORGANISM: Artificial sequence
<220> FEATURE:
<223> OTHER INFORMATION: engineered plasmid containining 201IA(H435)
      mutant
<220> FEATURE:
<221> NAME/KEY: misc_feature
<222> LOCATION: (275)..(404)
<223> OTHER INFORMATION: 3' ITR (complement)
<220> FEATURE:
<221> NAME/KEY: rep_origin
<222> LOCATION: (2198)..(2786)
<220> FEATURE:
<221> NAME/KEY: misc_feature
<222> LOCATION: (3226)..(3355)
<220> FEATURE:
<221> NAME/KEY: misc_feature
<222> LOCATION: (3423)..(3804)
<223> OTHER INFORMATION: CMV IE promoter
<220> FEATURE:
<221> NAME/KEY: promoter
<222> LOCATION: (3807)..(4088)
<223> OTHER INFORMATION: CB promoter
<220> FEATURE:
<221> NAME/KEY: TATA_signal
<222> LOCATION: (4061)..(4064)
<223> OTHER INFORMATION: rabbit globin polyA
<220> FEATURE:
<221> NAME/KEY: Intron
<222> LOCATION: (4183)..(5155)
<223> OTHER INFORMATION: chicken beta-actin intron
<220> FEATURE:
<221> NAME/KEY: CDS
<222> LOCATION: (5161)..(6690)
<223> OTHER INFORMATION: CMV IE promoter

<400> SEQUENCE: 5
```

-continued

```
gtacctctag agtcgacccg ggcggcctcg aggacggggt gaactacgcc tgaggatccg      60
atcttttttcc ctctgccaaa aattatgggg acatcatgaa gccccttgag catctgactt    120
ctggctaata aaggaaattt attttcattg caatagtgtg ttggaatttt ttgtgtctct    180
cactcggaag caattcgttg atctgaattt cgaccaccca taatacccat taccctggta    240
gataagtagc atggcgggtt aatcattaac tacaaggaac ccctagtgat ggagttggcc    300
actccctctc tgcgcgctcg ctcgctcact gaggccgggc gaccaaaggt cgcccgacgc    360
ccgggctttg cccgggcggc ctcagtgagc gagcgagcgc gcagccttaa ttaacctaat    420
tcactggccg tcgttttaca acgtcgtgac tgggaaaacc ctggcgttac ccaacttaat    480
cgccttgcag cacatccccc tttcgccagc tggcgtaata gcgaagaggc ccgcaccgat    540
cgcccttccc aacagttgcg cagcctgaat ggcgaatggg acgcgccctg tagcggcgca    600
ttaagcgcgg cgggtgtggt ggttacgcgc agcgtgaccg ctacacttgc cagcgcccta    660
gcgcccgctc ctttcgcttt cttcccttcc tttctcgcca cgttcgccgg ctttccccgt    720
caagctctaa atcgggggct ccctttaggg ttccgattta gtgctttacg gcacctcgac    780
cccaaaaaac ttgattaggg tgatggttca cgtagtgggc catcgccctg atagacggtt    840
tttcgccctt tgacgttgga gtccacgttc tttaatagtg gactcttgtt ccaaactgga    900
acaacactca accctatctc ggtctattct tttgatttat aagggatttt gccgatttcg    960
gcctattggt taaaaaatga gctgatttaa caaaaattta acgcgaattt taacaaaata   1020
ttaacgctta caatttaggt ggcacttttc ggggaaatgt gcgcggaacc cctatttgtt   1080
tatttttcta aatacattca aatatgtatc cgctcatgag acaataaccc tgataaatgc   1140
ttcaataata ttgaaaaagg aagagtatga gtattcaaca tttccgtgtc gcccttattc   1200
ccttttttgc ggcattttgc cttcctgttt ttgctcaccc agaaacgctg gtgaaagtaa   1260
aagatgctga agatcagttg ggtgcacgag tgggttacat cgaactggat ctcaacagcg   1320
gtaagatcct tgagagtttt cgccccgaag aacgttttcc aatgatgagc acttttaaag   1380
ttctgctatg tggcgcggta ttatcccgta ttgacgccgg gcaagagcaa ctcggtcgcc   1440
gcatacacta ttctcagaat gacttggttg agtactcacc agtcacagaa aagcatctta   1500
cggatggcat gacagtaaga gaattatgca gtgctgccat aaccatgagt gataacactg   1560
cggccaactt acttctgaca acgatcgagg accgaaggga gctaaccgct tttttgcaca   1620
acatggggga tcatgtaact cgccttgatc gttgggaacc ggagctgaat gaagccatac   1680
caaacgacga gcgtgacacc acgatgcctg tagcaatggc aacaacgttg cgcaaactat   1740
taactggcga actacttact ctagcttccc ggcaacaatt aatagactgg atggaggcgg   1800
ataaagttgc aggaccactt ctgcgctcgg cccttccggc tggctggttt attgctgata   1860
aatctggagc cggtgagcgt gggtctcgcg gtatcattgc agcactgggg ccagatggta   1920
agccctcccg tatcgtagtt atctacacga cggggagtca ggcaactatg gatgaacgaa   1980
atagacagat cgctgagata ggtgcctcac tgattaagca ttggtaactg tcagaccaag   2040
tttactcata tactttag attgatttaa aacttcattt ttaatttaaa aggatctagg   2100
tgaagatcct tttttgataat ctcatgacca aaatccctta acgtgagttt cgttccact   2160
gagcgtcaga ccccgtagaa aagatcaaag gatcttcttg agatcctttt tttctgcgcg   2220
taatctgctg cttgcaaaca aaaaaaccac cgctaccagc ggtggtttgt ttgccggatc   2280
aagagctacc aactctttt ccgaaggtaa ctggcttcag cagagcgcag ataccaaata   2340
```

```
ctgttcttct agtgtagccg tagttaggcc accacttcaa gaactctgta gcaccgccta    2400
catacctcgc tctgctaatc ctgttaccag tggctgctgc cagtggcgat aagtcgtgtc    2460
ttaccgggtt ggactcaaga cgatagttac cggataaggc gcagcggtcg ggctgaacgg    2520
ggggttcgtg cacacagccc agcttggagc gaacgaccta caccgaactg agatacctac    2580
agcgtgagct atgagaaagc gccacgcttc ccgaagggag aaaggcggac aggtatccgg    2640
taagcggcag ggtcggaaca ggagagcgca cgagggagct tccaggggga aacgcctggt    2700
atctttatag tcctgtcggg tttcgccacc tctgacttga gcgtcgattt ttgtgatgct    2760
cgtcaggggg gcggagccta tggaaaaacg ccagcaacgc ggccttttta cggttcctgg    2820
ccttttgctg gccttttgct cacatgttct ttcctgcgtt atcccctgat tctgtggata    2880
accgtattac cgcctttgag tgagctgata ccgctcgccg cagccgaacg accgagcgca    2940
gcgagtcagt gagcgaggaa gcggaagagc gcccaatacg caaaccgcct ctccccgcgc    3000
gttggccgat tcattaatgc agctggcacg acaggtttcc cgactggaaa gcgggcagtg    3060
agcgcaacgc aattaatgtg agttagctca ctcattaggc accccaggct ttacacttta    3120
tgcttccggc tcgtatgttg tgtggaattg tgagcggata acaatttcac acaggaaaca    3180
gctatgacca tgattacgcc agatttaatt aaggccttaa ttaggctgcg cgctcgctcg    3240
ctcactgagg ccgcccgggc aaagcccggg cgtcgggcga cctttggtcg cccggcctca    3300
gtgagcgagc gagcgcgcag agagggagtg gccaactcca tcactagggg ttccttgtag    3360
ttaatgatta cccgccatg ctacttatct accagggtaa tggggatcct ctagaactat    3420
agctagtcga cattgattat tgactagtta ttaatagtaa tcaattacgg ggtcattagt    3480
tcatagccca tatatggagt tccgcgttac ataacttacg gtaaatggcc cgcctggctg    3540
accgcccaac gacccccgcc cattgacgtc aataatgacg tatgttccca tagtaacgcc    3600
aatagggact ttccattgac gtcaatgggt ggactattta cggtaaactg cccacttggc    3660
agtacatcaa gtgtatcata tgccaagtac gccccctatt gacgtcaatg acggtaaatg    3720
gcccgcctgg cattatgccc agtacatgac cttatgggac tttcctactt ggcagtacat    3780
ctacgtatta gtcatcgcta ttaccatggt cgaggtgagc cccacgttct gcttcactct    3840
ccccatctcc cccccctccc cacccccaat tttgtattta tttatttttt aattattttg    3900
tgcagcgatg ggggcggggg ggggggggg gcgcgcgcca ggcggggcgg ggcggggcga    3960 ggggcgggc ggggcgaggc ggagaggtgc ggcggcagcc aatcagagcg gcgcgctccg    4020
aaagtttcct tttatggcga ggcggcggcg cggcggcccc tataaaaagc gaagcgcgcg    4080
gcgggcgggg agtcgctgcg acgctgcctt cgccccgtgc cccgctccgc cgccgcctcg    4140
cgccgcccgc cccggctctg actgaccgcg ttactcccac aggtgagcgg gcgggacggc    4200
ccttctcctc cgggctgtaa ttagcgcttg gtttaatgac ggcttgtttc ttttctgtgg    4260
ctgcgtgaaa gccttgaggg gctccgggag ggccctttgt gcgggggag cggctcgggg    4320 ggtgcgtgcg tgtgtgtgtg cgtggggagc gccgcgtgcg gctccgcgct gcccggcggc    4380
tgtgagcgct gcgggcgcgg cgcggggctt tgtgcgctcc gcagtgtgcg cgaggggagc    4440
gcggccgggg gcggtgcccc gcggtgcggg ggggctgcg agggaacaa aggctgcgtg    4500 cggggtgtgt gcgtggggg gtgagcaggg ggtgtgggcg cgtcggtcgg gctgcaaccc    4560
cccctgcacc cccctccccg agttgctgag cacggcccgg cttcgggtgc ggggctccgt    4620
acggggcgtg gcgcggggct cgccgtgccg ggcggggggt ggcggcaggt gggggtgccg    4680
ggcggggcgg ggccgcctcg ggccggggag ggctcgggg aggggcgcgg cggccccgg    4740
```

```
agcgccggcg gctgtcgagg cgcggcgagc cgcagccatt gccttttatg gtaatcgtgc   4800
gagagggcgc agggacttcc tttgtcccaa atctgtgcgg agccgaaatc tgggaggcgc   4860
cgccgcaccc cctctagcgg gcgcggggcg aagcggtgcg gcgccggcag gaaggaaatg   4920
ggcggggagg gccttcgtgc gtcgccgcgc cgccgtcccc ttctccctct ccagcctcgg   4980
ggctgtccgc ggggggacgg ctgccttcgg ggggacggg gcagggcggg gttcggcttc   5040
tggcgtgtga ccggcggctc tagagcctct gctaaccatg ttcatgcctt cttctttttc   5100
ctacagctcc tgggcaacgt gctggttatt gtgctgtctc atcattttgg caaagaattc   5160
```

| | | | | | | | | | | | | | | | | |
|---|---|---|---|---|---|---|---|---|---|---|---|---|---|---|---|---|
| atg | gag | ttc | ggg | ctg | agc | tgg | gtc | ttt | ctg | gtg | gcc | ctg | ctg | aag | gga | 5208 |
| Met | Glu | Phe | Gly | Leu | Ser | Trp | Val | Phe | Leu | Val | Ala | Leu | Leu | Lys | Gly | |
| 1 | | | | 5 | | | | | 10 | | | | | 15 | | |

| gtc | cag | tgc | gag | gtg | cag | ctg | ctg | gaa | tcc | gga | cct | ggc | ctg | gtg | aaa | 5256 |
|---|---|---|---|---|---|---|---|---|---|---|---|---|---|---|---|---|
| Val | Gln | Cys | Glu | Val | Gln | Leu | Leu | Glu | Ser | Gly | Pro | Gly | Leu | Val | Lys | |
| | | 20 | | | | | 25 | | | | | 30 | | | | |

| cca | tct | gag | aca | ctg | agt | ctg | act | tgt | gct | gtc | tcc | ggc | ctg | tct | atc | 5304 |
|---|---|---|---|---|---|---|---|---|---|---|---|---|---|---|---|---|
| Pro | Ser | Glu | Thr | Leu | Ser | Leu | Thr | Cys | Ala | Val | Ser | Gly | Leu | Ser | Ile | |
| | 35 | | | | | 40 | | | | | 45 | | | | | |

| agc | tcc | gat | ttc | tcc | tgg | gca | tgg | att | agg | cag | acc | ccc | ggc | aag | gcc | 5352 |
|---|---|---|---|---|---|---|---|---|---|---|---|---|---|---|---|---|
| Ser | Ser | Asp | Phe | Ser | Trp | Ala | Trp | Ile | Arg | Gln | Thr | Pro | Gly | Lys | Ala | |
| 50 | | | | | 55 | | | | | 60 | | | | | | |

| ctg | gaa | tat | gtg | ggg | tac | atc | cgc | ggg | aac | acc | gga | gat | aca | tac | tat | 5400 |
|---|---|---|---|---|---|---|---|---|---|---|---|---|---|---|---|---|
| Leu | Glu | Tyr | Val | Gly | Tyr | Ile | Arg | Gly | Asn | Thr | Gly | Asp | Thr | Tyr | Tyr | |
| 65 | | | | 70 | | | | | 75 | | | | | 80 | | |

| aat | cct | agt | ctg | aag | tca | agg | ctg | act | atc | tca | aag | gac | acc | agc | aaa | 5448 |
|---|---|---|---|---|---|---|---|---|---|---|---|---|---|---|---|---|
| Asn | Pro | Ser | Leu | Lys | Ser | Arg | Leu | Thr | Ile | Ser | Lys | Asp | Thr | Ser | Lys | |
| | | | | 85 | | | | | 90 | | | | | 95 | | |

| aac | caa | atc | tac | ctg | aat | ctg | tct | agt | gtc | acc | gct | ggc | gat | gcc | gcc | 5496 |
|---|---|---|---|---|---|---|---|---|---|---|---|---|---|---|---|---|
| Asn | Gln | Ile | Tyr | Leu | Asn | Leu | Ser | Ser | Val | Thr | Ala | Gly | Asp | Ala | Ala | |
| | | | 100 | | | | | 105 | | | | | 110 | | | |

| gtg | tac | tat | tgc | gca | agg | gac | cgg | gtg | tgc | gac | gat | gac | tac | gga | tac | 5544 |
|---|---|---|---|---|---|---|---|---|---|---|---|---|---|---|---|---|
| Val | Tyr | Tyr | Cys | Ala | Arg | Asp | Arg | Val | Cys | Asp | Asp | Asp | Tyr | Gly | Tyr | |
| | | 115 | | | | | 120 | | | | | 125 | | | | |

| tat | tac | acc | gag | gtg | tgc | ttc | ggc | ctg | gat | tct | tgg | ggg | cag | gga | atc | 5592 |
|---|---|---|---|---|---|---|---|---|---|---|---|---|---|---|---|---|
| Tyr | Tyr | Thr | Glu | Val | Cys | Phe | Gly | Leu | Asp | Ser | Trp | Gly | Gln | Gly | Ile | |
| | 130 | | | | | 135 | | | | | 140 | | | | | |

| gtg | gtc | aca | gtg | tca | agc | ggc | gga | gga | ggc | agc | gga | gga | gga | ggg | tcc | 5640 |
|---|---|---|---|---|---|---|---|---|---|---|---|---|---|---|---|---|
| Val | Val | Thr | Val | Ser | Ser | Gly | Gly | Gly | Gly | Ser | Gly | Gly | Gly | Gly | Ser | |
| 145 | | | | 150 | | | | | 155 | | | | | 160 | | |

| gga | ggc | ggg | gga | tct | gca | gaa | ctg | gtc | atg | aca | cag | tcc | cca | ctg | agc | 5688 |
|---|---|---|---|---|---|---|---|---|---|---|---|---|---|---|---|---|
| Gly | Gly | Gly | Gly | Ser | Ala | Glu | Leu | Val | Met | Thr | Gln | Ser | Pro | Leu | Ser | |
| | | | | 165 | | | | | 170 | | | | | 175 | | |

| ctg | tcc | gtc | gct | cca | gga | cag | act | gca | tct | att | agt | tgt | cga | tcc | tct | 5736 |
|---|---|---|---|---|---|---|---|---|---|---|---|---|---|---|---|---|
| Leu | Ser | Val | Ala | Pro | Gly | Gln | Thr | Ala | Ser | Ile | Ser | Cys | Arg | Ser | Ser | |
| | | | 180 | | | | | 185 | | | | | 190 | | | |

| cag | tcc | ctg | gac | tat | gct | aac | ggc | aat | acc | tac | ctg | tct | tgg | ttt | cac | 5784 |
|---|---|---|---|---|---|---|---|---|---|---|---|---|---|---|---|---|
| Gln | Ser | Leu | Asp | Tyr | Ala | Asn | Gly | Asn | Thr | Tyr | Leu | Ser | Trp | Phe | His | |
| | | | 195 | | | | | 200 | | | | | 205 | | | |

| cag | cga | cca | gga | cag | cca | cct | cgg | aga | ctg | atc | tat | cag | att | tcc | aac | 5832 |
|---|---|---|---|---|---|---|---|---|---|---|---|---|---|---|---|---|
| Gln | Arg | Pro | Gly | Gln | Pro | Pro | Arg | Arg | Leu | Ile | Tyr | Gln | Ile | Ser | Asn | |
| | 210 | | | | | 215 | | | | | 220 | | | | | |

| aga | gat | tct | gga | gtg | ccc | gac | agg | ttc | tca | ggc | agc | gga | gca | gga | act | 5880 |
|---|---|---|---|---|---|---|---|---|---|---|---|---|---|---|---|---|
| Arg | Asp | Ser | Gly | Val | Pro | Asp | Arg | Phe | Ser | Gly | Ser | Gly | Ala | Gly | Thr | |
| 225 | | | | 230 | | | | | 235 | | | | | 240 | | |

| gag | ttt | acc | ctg | cga | atc | agt | cgg | atg | gaa | tca | gat | gac | gtg | ggg | atc | 5928 |
|---|---|---|---|---|---|---|---|---|---|---|---|---|---|---|---|---|
| Glu | Phe | Thr | Leu | Arg | Ile | Ser | Arg | Met | Glu | Ser | Asp | Asp | Val | Gly | Ile | |
| | | | | 245 | | | | | 250 | | | | | 255 | | |

| | | | |
|---|---|---|---|
| tac tac tgc gga cag ggg acc aca ttc cca cgg aca ttt gga cag ggc<br>Tyr Tyr Cys Gly Gln Gly Thr Thr Phe Pro Arg Thr Phe Gly Gln Gly<br>260 265 270 | | | 5976 |
| act aag gtg gag atc aaa acc tgt gga gga gga agc aag cca cca acc<br>Thr Lys Val Glu Ile Lys Thr Cys Gly Gly Gly Ser Lys Pro Pro Thr<br>275 280 285 | | | 6024 |
| tgc cct cca tgt aca tct ccc gaa ctg ctg ggc ggg cct agc gtg ttc<br>Cys Pro Pro Cys Thr Ser Pro Glu Leu Leu Gly Gly Pro Ser Val Phe<br>290 295 300 | | | 6072 |
| ctg ttt ccc cct aag cct aaa gat aca ctg atg att agt aga acc cca<br>Leu Phe Pro Pro Lys Pro Lys Asp Thr Leu Met Ile Ser Arg Thr Pro<br>305 310 315 320 | | | 6120 |
| gag gtc aca tgc gtg gtc gtg gac gtg tcc cag gaa gat cct gac gtg<br>Glu Val Thr Cys Val Val Val Asp Val Ser Gln Glu Asp Pro Asp Val<br>325 330 335 | | | 6168 |
| aag ttc aac tgg tac gtg aat ggc gcc gag gtg cac cat gct cag act<br>Lys Phe Asn Trp Tyr Val Asn Gly Ala Glu Val His His Ala Gln Thr<br>340 345 350 | | | 6216 |
| aaa cca cgc gaa acc cag tat aat agt aca tac cga gtc gtg tca gtc<br>Lys Pro Arg Glu Thr Gln Tyr Asn Ser Thr Tyr Arg Val Val Ser Val<br>355 360 365 | | | 6264 |
| ctg aca gtg act cac cag gat tgg ctg aac ggc aag gag tat acc tgc<br>Leu Thr Val Thr His Gln Asp Trp Leu Asn Gly Lys Glu Tyr Thr Cys<br>370 375 380 | | | 6312 |
| aag gtg tct aac aag gcc ctg ccc gcc cct atc cag aaa aca att agc<br>Lys Val Ser Asn Lys Ala Leu Pro Ala Pro Ile Gln Lys Thr Ile Ser<br>385 390 395 400 | | | 6360 |
| aag gac aaa ggg cag cca cgg gaa ccc cag gtg tac act ctg cca ccc<br>Lys Asp Lys Gly Gln Pro Arg Glu Pro Gln Val Tyr Thr Leu Pro Pro<br>405 410 415 | | | 6408 |
| tca aga gag gaa ctg act aag aac cag gtc agc ctg acc tgt ctg gtg<br>Ser Arg Glu Glu Leu Thr Lys Asn Gln Val Ser Leu Thr Cys Leu Val<br>420 425 430 | | | 6456 |
| aaa ggc ttc tac ccc agc gat atc gtc gtg gag tgg gaa agt tca ggc<br>Lys Gly Phe Tyr Pro Ser Asp Ile Val Val Glu Trp Glu Ser Ser Gly<br>435 440 445 | | | 6504 |
| cag cct gag aat act tac aag act acc cct cca gtg ctg gat agc gac<br>Gln Pro Glu Asn Thr Tyr Lys Thr Thr Pro Pro Val Leu Asp Ser Asp<br>450 455 460 | | | 6552 |
| ggg tcc tat ttc ctg tac agc aag ctg aca gtg gac aaa tcc cgc tgg<br>Gly Ser Tyr Phe Leu Tyr Ser Lys Leu Thr Val Asp Lys Ser Arg Trp<br>465 470 475 480 | | | 6600 |
| cag cag gga aac gtc ttt tcc tgt tct gtg atg cat gag gcc ctg cac<br>Gln Gln Gly Asn Val Phe Ser Cys Ser Val Met His Glu Ala Leu His<br>485 490 495 | | | 6648 |
| aat gct tac acc cag aag agt ctg tca ctg agc ccc ggc aaa tgag<br>Asn Ala Tyr Thr Gln Lys Ser Leu Ser Leu Ser Pro Gly Lys<br>500 505 510 | | | 6694 |

<210> SEQ ID NO 6
<211> LENGTH: 510
<212> TYPE: PRT
<213> ORGANISM: Artificial sequence
<220> FEATURE:
<223> OTHER INFORMATION: Synthetic Construct

<400> SEQUENCE: 6

Met Glu Phe Gly Leu Ser Trp Val Phe Leu Val Ala Leu Leu Lys Gly
1               5                   10                  15

Val Gln Cys Glu Val Gln Leu Leu Glu Ser Gly Pro Gly Leu Val Lys
            20                  25                  30

-continued

Pro Ser Glu Thr Leu Ser Leu Thr Cys Ala Val Ser Gly Leu Ser Ile
    35                  40                  45

Ser Ser Asp Phe Ser Trp Ala Trp Ile Arg Gln Thr Pro Gly Lys Ala
50                  55                  60

Leu Glu Tyr Val Gly Tyr Ile Arg Gly Asn Thr Gly Asp Thr Tyr Tyr
65                  70                  75                  80

Asn Pro Ser Leu Lys Ser Arg Leu Thr Ile Ser Lys Asp Thr Ser Lys
                85                  90                  95

Asn Gln Ile Tyr Leu Asn Leu Ser Ser Val Thr Ala Gly Asp Ala Ala
            100                 105                 110

Val Tyr Tyr Cys Ala Arg Asp Arg Val Cys Asp Asp Tyr Gly Tyr
            115                 120                 125

Tyr Tyr Thr Glu Val Cys Phe Gly Leu Asp Ser Trp Gly Gln Gly Ile
        130                 135                 140

Val Val Thr Val Ser Ser Gly Gly Gly Ser Gly Gly Gly Ser
145                 150                 155                 160

Gly Gly Gly Gly Ser Ala Glu Leu Val Met Thr Gln Ser Pro Leu Ser
                165                 170                 175

Leu Ser Val Ala Pro Gly Gln Thr Ala Ser Ile Ser Cys Arg Ser Ser
            180                 185                 190

Gln Ser Leu Asp Tyr Ala Asn Gly Asn Thr Tyr Leu Ser Trp Phe His
        195                 200                 205

Gln Arg Pro Gly Gln Pro Arg Arg Leu Ile Tyr Gln Ile Ser Asn
    210                 215                 220

Arg Asp Ser Gly Val Pro Asp Arg Phe Ser Gly Ser Ala Gly Thr
225                 230                 235                 240

Glu Phe Thr Leu Arg Ile Ser Arg Met Glu Ser Asp Asp Val Gly Ile
                245                 250                 255

Tyr Tyr Cys Gly Gln Gly Thr Thr Phe Pro Arg Thr Phe Gly Gln Gly
            260                 265                 270

Thr Lys Val Glu Ile Lys Thr Cys Gly Gly Gly Ser Lys Pro Pro Thr
        275                 280                 285

Cys Pro Pro Cys Thr Ser Pro Glu Leu Leu Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser Gln Glu Asp Pro Asp Val
                325                 330                 335

Lys Phe Asn Trp Tyr Val Asn Gly Ala Glu Val His His Ala Gln Thr
            340                 345                 350

Lys Pro Arg Glu Thr Gln Tyr Asn Ser Thr Tyr Arg Val Val Ser Val
        355                 360                 365

Leu Thr Val Thr His Gln Asp Trp Leu Asn Gly Lys Glu Tyr Thr Cys
    370                 375                 380

Lys Val Ser Asn Lys Ala Leu Pro Ala Pro Ile Gln Lys Thr Ile Ser
385                 390                 395                 400

Lys Asp Lys Gly Gln Pro Arg Glu Pro Gln Val Tyr Thr Leu Pro Pro
                405                 410                 415

Ser Arg Glu Glu Leu Thr Lys Asn Gln Val Ser Leu Thr Cys Leu Val
            420                 425                 430

Lys Gly Phe Tyr Pro Ser Asp Ile Val Val Glu Trp Glu Ser Ser Gly
        435                 440                 445

```
Gln Pro Glu Asn Thr Tyr Lys Thr Thr Pro Pro Val Leu Asp Ser Asp
        450                 455                 460

Gly Ser Tyr Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn Ala Tyr Thr Gln Lys Ser Leu Ser Leu Ser Pro Gly Lys
                500                 505                 510

<210> SEQ ID NO 7
<211> LENGTH: 819
<212> TYPE: DNA
<213> ORGANISM: Artificial sequence
<220> FEATURE:
<223> OTHER INFORMATION: engineered aducanumab scFv coding sequence

<400> SEQUENCE: 7
atgtacaaga tgcagctgct gagctgtatc gccctgaccc tggtgctggt ggccaactct      60
caggtgcagc tggtggaatc tggcggcgga gtggtgcagc tggcagaag cctgagactg     120 agctgtgccg ccagcggctt cgccttcagc agctacggaa tgcactgggt cgccaggcc     180 cctggcaaag actggaatg ggtggccgtg atttggttcg acggcaccaa gaagtactac     240
accgacagcg tgaagggccg gttcaccatc agccgggaca acagcaagaa caccctgtac     300
ctgcagatga taccctgcg ggccgaggac accgccgtgt actactgcgc cagagacaga     360
ggcatcggcg ccagacgggg cccttactac atggacgtgt ggggcaaggg caccaccgtg     420
acagtgtctg gcggaggcgg aagtggcgga ggggatcag gcggggaggg cagcgatatt     480
cagatgaccc agagccccag cagcctgagc gcctctgtgg gcgacagagt gaccatcacc     540
tgtcgggcca gcagagcat cagctcctac ctgaactggt atcagcagaa gcccggcaag     600
gcccccaagc tgctgatcta tgccgcctcc agtctgcaga gcggcgtgcc cagcagattt     660
tctggcagcg gctccggcac cgacttcacc ctgacaatca gctccctgca gcccgaggac     720
ttcgccacct actactgcca gcagagctac agcaccccc tgacattcgg cggaggcacc     780
aaggtggaaa tcaagcacca ccaccatcac cactgatga                            819

<210> SEQ ID NO 8
<211> LENGTH: 271
<212> TYPE: PRT
<213> ORGANISM: Artificial sequence
<220> FEATURE:
<223> OTHER INFORMATION: Aducanumab scFv construct amino acid sequence
<220> FEATURE:
<221> NAME/KEY: SIGNAL
<222> LOCATION: (1)..(20)
<223> OTHER INFORMATION: IL2 secretion signal
<220> FEATURE:
<221> NAME/KEY: MISC_FEATURE
<222> LOCATION: (21)..(143)
<220> FEATURE:
<221> NAME/KEY: MISC_FEATURE
<222> LOCATION: (144)..(158)
<223> OTHER INFORMATION: Gly-Ser Llinker
<220> FEATURE:
<221> NAME/KEY: MISC_FEATURE
<222> LOCATION: (159)..(265)
<223> OTHER INFORMATION: Light Variable region
<220> FEATURE:
<221> NAME/KEY: MISC_FEATURE
<222> LOCATION: (266)..(271)
<223> OTHER INFORMATION: 6xHistag (Explasy)

<400> SEQUENCE: 8
```

Met Tyr Lys Met Gln Leu Leu Ser Cys Ile Ala Leu Thr Leu Val Leu
1               5                   10                  15

Val Ala Asn Ser Gln Val Gln Leu Val Glu Ser Gly Gly Gly Val Val
            20                  25                  30

Gln Pro Gly Arg Ser Leu Arg Leu Ser Cys Ala Ala Ser Gly Phe Ala
        35                  40                  45

Phe Ser Ser Tyr Gly Met His Trp Val Arg Gln Ala Pro Gly Lys Gly
    50                  55                  60

Leu Glu Trp Val Ala Val Ile Trp Phe Asp Gly Thr Lys Lys Tyr Tyr
65                  70                  75                  80

Thr Asp Ser Val Lys Gly Arg Phe Thr Ile Ser Arg Asp Asn Ser Lys
                85                  90                  95

Asn Thr Leu Tyr Leu Gln Met Asn Thr Leu Arg Ala Glu Asp Thr Ala
            100                 105                 110

Val Tyr Tyr Cys Ala Arg Asp Arg Gly Ile Gly Ala Arg Arg Gly Pro
        115                 120                 125

Tyr Tyr Met Asp Val Trp Gly Lys Gly Thr Thr Val Thr Val Ser Gly
    130                 135                 140

Gly Gly Gly Ser Gly Gly Gly Ser Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Ser Ile Ser Ser Tyr Leu Asn
            180                 185                 190

Trp Tyr Gln Gln Lys Pro Gly Lys Ala Pro Lys Leu Leu Ile Tyr Ala
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Ser Tyr Ser Thr Pro Leu Thr Phe
                245                 250                 255

Gly Gly Gly Thr Lys Val Glu Ile Lys His His His His His His
            260                 265                 270

<210> SEQ ID NO 9
<211> LENGTH: 798
<212> TYPE: DNA
<213> ORGANISM: Artificial Sequence
<220> FEATURE:
<223> OTHER INFORMATION: Engineered crenezumab scFv construct

<400> SEQUENCE: 9
atgtacaaga tgcagctgct gagctgtatc gccctgaccc tggtgctggt ggccaactct      60
gaagtgcagc tggtggaaag cggcggaggc ctggtgcagc ctggcggatc tctgagactg     120
agctgtgccg ccagcggctt caccttcagc agctacggca tgagctgggt cgcccaggcc     180
cctggaaaag gcctggaact ggtggcctcc atcaacagca tggcggcag cacctactac     240 cccgacagcg tgaagggccg gttcaccatc tcccgggaca cgccaagaa cagcctgtac     300 ctgcagatga actccctgcg ggccgaggac accgccgtgt actattgtgc cagcggcgac     360
tattggggcc agggcacaac cgtgacagtg tctggcggag gcggatctgg gggcggagga     420
tcaggcgggg gaggatctga tatcgtgatg acccagagcc ccctgagcct gcctgtgaca     480
cctggcgaac tgccagcat cagctgcaga tccagcaga gcctggtgta cagcaacggc     540

```
gacacctacc tgcactggta tctgcagaag cccggccaga gccctcagct gctgatctac    600
aaggtgtcca accggttcag cggcgtgccc gacagatttt ctggcagcgg ctccggcacc    660
gacttcaccc tgaagatcag ccgggtggaa gccgaggacg tgggcgtgta ctactgcagc    720
cagtccaccc acgtgccctg gacatttgga cagggcacca aggtggaaat caagcaccac    780
caccatcacc actgatga                                                   798
```

```
<210> SEQ ID NO 10
<211> LENGTH: 264
<212> TYPE: PRT
<213> ORGANISM: Artificial sequence
<220> FEATURE:
<223> OTHER INFORMATION: Engineered Crenezumab scFv  amino acid sequence
<220> FEATURE:
<221> NAME/KEY: SIGNAL
<222> LOCATION: (1)..(20)
<223> OTHER INFORMATION: IL-2 secretion signal
<220> FEATURE:
<221> NAME/KEY: MISC_FEATURE
<222> LOCATION: (21)..(131)
<223> OTHER INFORMATION: Heavy variable region
<220> FEATURE:
<221> NAME/KEY: MISC_FEATURE
<222> LOCATION: (131)..(146)
<223> OTHER INFORMATION: Gly-Ser Linker
<220> FEATURE:
<221> NAME/KEY: MISC_FEATURE
<222> LOCATION: (147)..(258)
<223> OTHER INFORMATION: Light Variable Region
<220> FEATURE:
<221> NAME/KEY: MISC_FEATURE
<222> LOCATION: (259)..(264)
<223> OTHER INFORMATION: 6xHis tag

<400> SEQUENCE: 10

Met Tyr Lys Met Gln Leu Leu Ser Cys Ile Ala Leu Thr Leu Val Leu
1               5                   10                  15

Val Ala Asn Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Gly Met Ser Trp Val Arg Gln Ala Pro Gly Lys Gly
    50                  55                  60

Leu Glu Leu Val Ala Ser Ile Asn Ser Asn Gly Gly Ser Thr Tyr Tyr
65                  70                  75                  80

Pro Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Ser Gly Asp Tyr Trp Gly Gln Gly Thr Thr Val
        115                 120                 125

Thr Val Ser Gly Gly Gly Gly Ser Gly Gly Gly Gly Ser Gly Gly Gly
    130                 135                 140

Gly Ser Asp Ile Val Met Thr Gln Ser Pro Leu Ser Leu Pro Val Thr
145                 150                 155                 160

Pro Gly Glu Pro Ala Ser Ile Ser Cys Arg Ser Ser Gln Ser Leu Val
                165                 170                 175

Tyr Ser Asn Gly Asp Thr Tyr Leu His Trp Tyr Leu Gln Lys Pro Gly
            180                 185                 190

Gln Ser Pro Gln Leu Leu Ile Tyr Lys Val Ser Asn Arg Phe Ser Gly
        195                 200                 205
```

-continued

```
Val Pro Asp Arg Phe Ser Gly Ser Gly Ser Gly Thr Asp Phe Thr Leu
    210                 215                 220
Lys Ile Ser Arg Val Glu Ala Glu Asp Val Gly Val Tyr Tyr Cys Ser
225                 230                 235                 240
Gln Ser Thr His Val Pro Trp Thr Phe Gly Gln Gly Thr Lys Val Glu
                245                 250                 255
Ile Lys His His His His His His
            260
```

```
<210> SEQ ID NO 11
<211> LENGTH: 798
<212> TYPE: DNA
<213> ORGANISM: Artificial Sequence
<220> FEATURE:
<223> OTHER INFORMATION: engineered Solanezumab scFv construct nucleic
      acid sequence:

<400> SEQUENCE: 11
atgtacaaga tgcagctgct gagctgtatc gccctgaccc tggtgctggt ggccaactct      60
gaagtgcagc tggtggaaag cggcggaggc ctggtgcagc ctggcggatc tctgagactg     120
agctgtgccg ccagcggctt caccttcagc cggtacagca tgagctgggt gcgccaggcc     180
cctggcaaag gactggaact ggtggcccag atcaacagcg tgggcaacag cacctactac     240
cccgacaccg tgaagggccg gttcaccatc agcagagaca acgccaagaa caccctgtac     300
ctgcagatga acagcctgcg ggccgaggac accgccgtgt actattgtgc cagcggcgac     360
tattggggcc agggcacact cgtgacagtg tctggcggag gcggatctgg gggcggagga     420
tcaggcgggg gaggatctga tgtcgtgatg acccagagcc ccctgagcct gcctgtgaca     480
ctgggacagc ctgccagcat cagctgcaga agcagccaga gcctgatcta cagcgacggc     540
aacgcctacc tgcactggtt tctgcagaaa cccggccagt cccccagact gctgatctat     600
aaggtgtcca accggttcag cggcgtgccc gacagatttt ctggcagcgg ctccggcacc     660
gacttcaccc tgaagatcag ccgggtggaa gccgaggacg tgggcgtgta ctactgcagc     720
cagtccaccc acgtgccctg gacatttgga cagggcacca aggtggaaat caagcaccac     780
caccatcacc actgatga                                                   798
```

```

<210> SEQ ID NO 12
<211> LENGTH: 264
<212> TYPE: PRT
<213> ORGANISM: Artificial Sequence
<220> FEATURE:
<223> OTHER INFORMATION: engineered Solanezumab scFv construct amino
      acid sequence
<220> FEATURE:
<221> NAME/KEY: SIGNAL
<222> LOCATION: (1)..(20)
<223> OTHER INFORMATION: IL2 secretion signal
<220> FEATURE:
<221> NAME/KEY: MISC_FEATURE
<222> LOCATION: (21)..(131)
<223> OTHER INFORMATION: Heavy chain variable
<220> FEATURE:
<221> NAME/KEY: MISC_FEATURE
<222> LOCATION: (132)..(146)
<220> FEATURE:
<221> NAME/KEY: MISC_FEATURE
<222> LOCATION: (147)..(258)
<223> OTHER INFORMATION: Variable Light Region
<220> FEATURE:
<221> NAME/KEY: MISC_FEATURE
<222> LOCATION: (259)..(264)
<223> OTHER INFORMATION: 6xHis tag
```

<400> SEQUENCE: 12

```
Met Tyr Lys Met Gln Leu Leu Ser Cys Ile Ala Leu Thr Leu Val Leu
1               5                   10                  15

Val Ala Asn Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Arg Tyr Ser Met Ser Trp Val Arg Gln Ala Pro Gly Lys Gly
    50                  55                  60

Leu Glu Leu Val Ala Gln Ile Asn Ser Val Gly Asn Ser Thr Tyr Tyr
65                  70                  75                  80

Pro Asp Thr Val Lys Gly Arg Phe Thr Ile Ser Arg Asp Asn Ala Lys
                85                  90                  95

Asn Thr Leu Tyr Leu Gln Met Asn Ser Leu Arg Ala Glu Asp Thr Ala
            100                 105                 110

Val Tyr Tyr Cys Ala Ser Gly Asp Tyr Trp Gly Gln Gly Thr Leu Val
        115                 120                 125

Thr Val Ser Gly Gly Gly Gly Ser Gly Gly Gly Gly Ser Gly Gly Gly
130                 135                 140

Gly Ser Asp Val Val Met Thr Gln Ser Pro Leu Ser Leu Pro Val Thr
145                 150                 155                 160

Leu Gly Gln Pro Ala Ser Ile Ser Cys Arg Ser Ser Gln Ser Leu Ile
                165                 170                 175

Tyr Ser Asp Gly Asn Ala Tyr Leu His Trp Phe Leu Gln Lys Pro Gly
            180                 185                 190

Gln Ser Pro Arg Leu Leu Ile Tyr Lys Val Ser Asn Arg Phe Ser Gly
        195                 200                 205

Val Pro Asp Arg Phe Ser Gly Ser Gly Thr Asp Phe Thr Leu
    210                 215                 220

Lys Ile Ser Arg Val Glu Ala Glu Asp Val Gly Val Tyr Tyr Cys Ser
225                 230                 235                 240

Gln Ser Thr His Val Pro Trp Thr Phe Gly Gln Gly Thr Lys Val Glu
                245                 250                 255

Ile Lys His His His His His His
            260
```

<210> SEQ ID NO 13
<211> LENGTH: 3165
<212> TYPE: DNA
<213> ORGANISM: Artificial sequence
<220> FEATURE:
<223> OTHER INFORMATION: AAV vector genome CB7.CI.aducanumabscFvRBG
<220> FEATURE:
<221> NAME/KEY: repeat_region
<222> LOCATION: (1)..(130)
<223> OTHER INFORMATION: 5" AAV2-ITR
<220> FEATURE:
<221> NAME/KEY: repeat_region
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(838)
<220> FEATURE:
<221> NAME/KEY: Intron
<222> LOCATION: (958)..(1930)
<223> OTHER INFORMATION: chicken beta actin promoter

```
<220> FEATURE:
<221> NAME/KEY: misc_feature
<222> LOCATION: (1958)..(2001)
<220> FEATURE:
<221> NAME/KEY: misc_feature
<222> LOCATION: (2002)..(2370)
<223> OTHER INFORMATION: aducanumab heavy variable region
<220> FEATURE:
<221> NAME/KEY: misc_feature
<222> LOCATION: (2371)..(2415)
<223> OTHER INFORMATION: Gly-Ser Linker
<220> FEATURE:
<221> NAME/KEY: misc_feature
<222> LOCATION: (2416)..(2736)
<223> OTHER INFORMATION: aducanumab light chain variable
<220> FEATURE:
<221> NAME/KEY: misc_feature
<222> LOCATION: (2737)..(2754)
<223> OTHER INFORMATION: His Tag
<220> FEATURE:
<221> NAME/KEY: polyA_signal
<222> LOCATION: (2821)..(2947)
<223> OTHER INFORMATION: Rabbit globulin polya
<220> FEATURE:
<221> NAME/KEY: repeat_region
<222> LOCATION: (3036)..(3165)
<223> OTHER INFORMATION: 3' ITR

<400> SEQUENCE: 13
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggact atttacggta     420
aactgcccac ttggcagtac atcaagtgta tcatatgcca gtacgccccc ctattgacgt     480
caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccccc ctccccaccc ccaattttgt atttatttat     660
tttttaatta ttttgtgcag cgatggggggc ggggggggggg ggggggcgcg cgccaggcgg     720
ggcggggcgg ggcgaggggc ggggcgggc gaggcggaga ggtgcggcgg cagccaatca     780
gagcggcgcg ctccgaaagt ttccttttat ggcgaggcgg cggcggcggc ggccctataa     840
aaagcgaagc gcgcggcggg cggggagtcg ctgcgacgct gccttcgccc cgtgccccgc     900
tccgccgccg cctcgcgccg cccgcccggg ctctgactga ccgcgttact cccacaggtg     960
agcgggcggg acggcccttc tcctccgggc tgtaattagc gcttggttta atgacggctt    1020
gtttcttttc tgtggctgcg tgaaagcctt gaggggctcc ggagggccc tttgtgcggg    1080 gggagcggct cggggggtgc gtgcgtgtgt gtgtgcgtgg ggagcgccgc gtgcggctcc    1140
gcgctgcccg gcggctgtga gcgctgcggg cgcggcgcgg ggctttgtgc gctccgcagt    1200
gtgcgcgagg ggagcgcggc cggggcggt gccccgcgt gcgggggggg ctgcgagggg     1260
aacaaaggct gcgtgcgggg tgtgtgcgtg ggggggtgag caggggggtgt gggcgcgtcg    1320 gtcgggctgc aacccccccct gcacccccct ccccgagttg ctgagcacgg cccggcttcg    1380
ggtgcggggc tccgtacggg gcgtggcgcg gggctcgccg tgccgggcgg ggggtggcgg    1440
caggtggggg tgccgggcgg ggcggggccg cctcgggccg gggagggctc ggggagggg    1500
```

```
cgcggcggcc cccggagcgc cggcggctgt cgaggcgcgg cgagccgcag ccattgcctt    1560
ttatggtaat cgtgcgagag ggcgcaggga cttcctttgt cccaaatctg tgcggagccg    1620
aaatctggga ggcgccgccg caccccctct agcgggcgcg gggcgaagcg gtgcggcgcc    1680
ggcaggaagg aaatgggcgg ggagggcctt cgtgcgtcgc cgcgccgccg tccccttctc    1740
cctctccagc ctcggggctg tccgcggggg gacggctgcc ttcgggggg acgggcagg     1800 gcggggttcg gcttctggcg tgtgaccggc ggctctagag cctctgctaa ccatgttcat    1860
gccttcttct ttttcctaca gctcctgggc aacgtgctgg ttattgtgct gtctcatcat    1920
tttggcaaag aattcgccac catgtacaag atgcagctgc tgagctgtat cgccctgacc    1980
ctggtgctgg tggccaactc tcaggtgcag ctggtggaat ctggcggcgg agtggtgcag    2040
cctggcagaa gcctgagact gagctgtgcc gccagcggct tcgccttcag cagctacgga    2100
atgcactggg tgcgccaggc ccctggcaaa ggactggaat gggtggccgt gatttggttc    2160
gacggcacca gaagtactac accgacagc gtgaagggcc ggttcaccat cagccgggac    2220
aacagcaaga acaccctgta cctgcagatg aatacccctgc gggccgagga caccgccgtg    2280
tactactgcg ccagagacag aggcatcggc gccagacggg gcccttacta catgacgtg     2340 tggggcaagg gcaccaccgt gacagtgtct ggcggaggcg gaagtggcgg aggggatca    2400 ggcggggag gcagcgatat tcagatgacc cagagcccca gcagcctgag cgcctctgtg    2460
ggcgacagag tgaccatcac ctgtcgggcc agccagagca tcagctccta cctgaactgg    2520
tatcagcaga agcccggcaa ggcccccaag ctgctgatct atgccgcctc cagtctgcag    2580
agcggcgtgc ccagcagatt ttctggcagc ggctccggca ccgacttcac cctgacaatc    2640
agctccctgc agcccgagga cttcgccacc tactactgcc agcagagcta cagcaccccc    2700
ctgacattcg gcggaggcac caaggtggaa atcaagcacc accaccatca ccactgatga    2760
ggtacctcta gagtcgaccc gggcggcctc gaggacgggg tgaactacgc ctgaggatcc    2820
gatctttttc cctctgccaa aaattatggg gacatcatga agccccttga gcatctgact    2880
tctggctaat aaaggaaatt tattttcatt gcaatagtgt gttggaatt tttgtgtctc    2940 tcactcggaa gcaattcgtt gatctgaatt tcgaccaccc ataatacca ttaccctggt     3000 agataagtag catggcgggt taatcattaa ctacaaggaa ccccctagtga tggagttggc    3060 cactccctct ctgcgcgctc gctcgctcac tgaggccggg cgaccaaagg tcgcccgacg    3120
cccgggcttt gcccgggcgg cctcagtgag cgagcgagcg cgcag                    3165
```

<210> SEQ ID NO 14
<211> LENGTH: 3144
<212> TYPE: DNA
<213> ORGANISM: Artificial sequence
<220> FEATURE:
<223> OTHER INFORMATION: pAAV.CB7.CI.crenezumabScFv.RBG
<220> FEATURE:
<221> NAME/KEY: repeat_region
<222> LOCATION: (1)..(130)
<223> OTHER INFORMATION: AAV2 - 5' ITR
<220> FEATURE:
<221> NAME/KEY: repeat_region
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(839)

```
<220> FEATURE:
<221> NAME/KEY: Intron
<222> LOCATION: (958)..(1930)
<220> FEATURE:
<221> NAME/KEY: misc_feature
<222> LOCATION: (1942)..(2001)
<223> OTHER INFORMATION: IL-2 secretion signal
<220> FEATURE:
<221> NAME/KEY: misc_feature
<222> LOCATION: (2001)..(2334)
<223> OTHER INFORMATION: crenezumab heavy variable region
<220> FEATURE:
<221> NAME/KEY: misc_feature
<222> LOCATION: (2335)..(2379)
<223> OTHER INFORMATION: Gly-Ser linker
<220> FEATURE:
<221> NAME/KEY: misc_feature
<222> LOCATION: (2380)..(2715)
<223> OTHER INFORMATION: crenezumab varalbe region light
<220> FEATURE:
<221> NAME/KEY: misc_feature
<222> LOCATION: (2716)..(2733)
<223> OTHER INFORMATION: His tag
<220> FEATURE:
<221> NAME/KEY: polyA_signal
<222> LOCATION: (2800)..(2926)
<223> OTHER INFORMATION: rabbit globin polyA
<220> FEATURE:
<221> NAME/KEY: repeat_region
<222> LOCATION: (3015)..(3144)
<223> OTHER INFORMATION: AAV2 - 3' ITR

<400> SEQUENCE: 14
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggact atttacggta     420
aactgcccac ttggcagtac atcaagtgta tcatatgcca gtacgccccc ctattgacgt     480
caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccc ctccccaccc ccaattttgt atttatttat     660
tttttaatta ttttgtgcag cgatggggc ggggggggg gggggcgcg cgccaggcgg     720 ggcggggcgg ggcgagggc ggggcgggc gaggcggaga ggtgcggcgg cagccaatca     780
gagcggcgcg ctccgaaagt ttcctttat ggcgaggcgg cggcggcggc ggccctataa     840
aaagcgaagc gcgcggcggg cggggagtcg ctgcgacgct gccttcgccc cgtgccccgc     900
tccgccgccg cctcgcgccg cccgccccgg ctctgactga ccgcgttact cccacaggtg     960
agcgggcggg acggcccttc tcctccgggc tgtaattagc gcttggttta atgacggctt    1020
gtttcttttc tgtggctgcg tgaaagcctt gaggggctcc gggagggccc tttgtgcggg    1080
gggagcggct cggggggtgc gtgcgtgtgt gtgtgcgtgg ggagcgccgc gtgcggctcc    1140
gcgctgcccg gcggctgtga gcgctgcggg cgcgcgcgg gctttgtgc gctccgcagt    1200 gtgcgcgagg ggagcgcggc cggggcggg gccccgcggt gcgggggggg ctgcgagggg    1260
aacaaaggct gcgtgcgggg tgtgtgcgtg ggggggtgag caggggtgt gggcgcgtcg    1320 gtcgggctgc aacccccct gcaccccct cccgagttg ctgagcacgg cccggcttcg    1380
```

```
ggtgcgggc   tccgtacggg  gcgtggcgcg  gggctcgccg  tgccgggcgg  ggggtggcgg    1440
caggtggggg  tgccgggcgg  ggcggggccg  cctcggccgc  gggagggctc  ggggagggg    1500 cgcggcggcc  cccggagcgc  cggcggctgt  cgaggcgcgg  cgagccgcag  ccattgcctt    1560
ttatggtaat  cgtgcgagag  ggcgcaggga  cttcctttgt  cccaaatctg  tgcggagccg    1620
aaatctggga  ggcgccgccg  caccccctct  agcgggcgcg  gggcgaagcg  gtgcggcgcc    1680
ggcaggaagg  aaatgggcgg  ggagggcctt  cgtgcgtcgc  cgcgccgccg  tcccttctc    1740 cctctccagc  tcggggctg   tccgcggggg  gacggctgcc  ttcgggggg   acgggcagg    1800 gcggggttcg  gcttctggcg  tgtgaccggc  ggctctagag  cctctgctaa  ccatgttcat    1860
gccttcttct  ttttcctaca  gctcctgggc  aacgtgctgg  ttattgtgct  gtctcatcat    1920
tttggcaaag  aattcgccac  catgtacaag  atgcagctgc  tgagctgtat  cgccctgacc    1980
ctggtgctgg  tggccaactc  tgaagtgcag  ctggtggaaa  gcggcggagg  cctggtgcag    2040
cctggcggat  ctctgagact  gagctgtgcc  gccagcggct  tcaccttcag  cagctacggc    2100
atgagctggg  tgcgccaggc  cctggaaaa   ggcctggaac  tggtggcctc  catcaacagc    2160
aatggcggca  gcacctacta  ccccgacagc  gtgaagggcc  ggttcaccat  ctcccgggac    2220
aacgccaaga  acagcctgta  cctgcagatg  aactccctgc  gggccgagga  caccgccgtg    2280
tactattgtg  ccagcggcga  ctattggggc  cagggcacaa  ccgtgacagt  gtctggcgga    2340
ggcggatctg  ggggcggagg  atcaggcggg  ggaggatctg  atatcgtgat  gacccagagc    2400
cccctgagcc  tgcctgtgac  acctggcgaa  cctgccagca  tcagctgcag  atccagccag    2460
agcctggtgt  acagcaacgg  cgacacctac  ctgcactggt  atctgcagaa  gcccggccag    2520
agccctcagc  tgctgatcta  caaggtgtcc  aaccggttca  gcggcgtgcc  cgacagattt    2580
tctggcagcg  gctccggcac  cgacttcacc  ctgaagatca  gccgggtgga  agccgaggac    2640
gtgggcgtgt  actactgcag  ccagtccacc  cacgtgccct  ggacatttgg  acagggcacc    2700
aaggtggaaa  tcaagcacca  ccaccatcac  cactgatgag  gtacctctag  agtcgacccg    2760
ggcggcctcg  aggacggggt  gaactacgcc  tgaggatccg  atcttttcc   ctctgccaaa    2820 aattatgggg  acatcatgaa  gccccttgag  catctgactt  ctggctaata  aaggaaattt    2880
attttcattg  caatagtgtg  ttggaatttt  ttgtgtctct  cactcggaag  caattcgttg    2940
atctgaattt  cgaccaccca  taatacccat  taccctggta  gataagtagc  atggcgggtt    3000
aatcattaac  tacaaggaac  ccctagtgat  ggagttggcc  actccctctc  tgcgcgctcg    3060
ctcgctcact  gaggccgggc  gaccaaaggt  cgcccgacgc  ccgggctttg  cccgggcggc    3120
ctcagtgagc  gagcgagcgc  gcag                                             3144
```

<210> SEQ ID NO 15
<211> LENGTH: 3144
<212> TYPE: DNA
<213> ORGANISM: Artificial Sequence
<220> FEATURE:
<223> OTHER INFORMATION: pAAV.CB7.CI.solanezumabscFv.RBG
<220> FEATURE:
<221> NAME/KEY: repeat_region
<222> LOCATION: (1)..(130)
<223> OTHER INFORMATION: AAV2 - 5' ITR
<220> FEATURE:
<221> NAME/KEY: repeat_region
<222> LOCATION: (198)..(579)
<223> OTHER INFORMATION: CMV IE promoter
<220> FEATURE:
<221> NAME/KEY: promoter
<222> LOCATION: (582)..(863)

```
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (958)..(1930)
<223> OTHER INFORMATION: chicken beta-actin intron
<220> FEATURE:
<221> NAME/KEY: misc_feature
<222> LOCATION: (1942)..(2001)
<223> OTHER INFORMATION: IL-2 secretion signal
<220> FEATURE:
<221> NAME/KEY: misc_feature
<222> LOCATION: (2002)..(2334)
<223> OTHER INFORMATION: solanezumab heavy variable region
<220> FEATURE:
<221> NAME/KEY: misc_feature
<222> LOCATION: (2335)..(2379)
<223> OTHER INFORMATION: Gly-Ser Linker
<220> FEATURE:
<221> NAME/KEY: misc_feature
<222> LOCATION: (2380)..(2715)
<223> OTHER INFORMATION: solanezumab light chain variable region
<220> FEATURE:
<221> NAME/KEY: polyA_signal
<222> LOCATION: (2800)..(2926)
<223> OTHER INFORMATION: rabbit globin polyA
<220> FEATURE:
<221> NAME/KEY: misc_feature
<222> LOCATION: (3015)..(3144)
<223> OTHER INFORMATION: AAV2 - 3' ITR

<400> SEQUENCE: 15
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag gtaatgggg     180 atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggact atttacggta     420
aactgcccac ttggcagtac atcaagtgta tcatatgcca agtacgcccc ctattgacgt     480
caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctccccccc ctccccaccc ccaattttgt atttatttat     660
tttttaatta ttttgtgcag cgatggggc ggggggggg gggggcgcg cgccaggcgg     720 ggcggggcgg ggcgaggggc ggggcggggc gaggcggaga ggtgcggcgg cagccaatca     780
gagcggcgcg ctccgaaagt tcctttttat ggcgaggcgg cggcggcggc ggccctataa     840
aaagcgaagc gcgcggcggg cggggagtcg ctgcgacgct gccttcgccc cgtgccccgc     900
tccgccgccg cctcgcgccg cccgccccgg ctctgactga ccgcgttact cccacaggtg     960
agcgggcggg acggcccttc tcctccgggc tgtaattagc gcttggttta atgacggctt    1020
gtttcttttc tgtggctgcg tgaaagcctt gaggggctcc gggagggccc tttgtgcggg    1080
gggagcggct cggggggtgc gtgcgtgtgt gtgtgcgtgg ggagcgccgc gtgcggctcc    1140
gcgctgcccg gcggctgtga gcgctgcggg cgcggcgcgg ggctttgtgc gctccgcagt    1200
gtgcgcgagg ggagcgcggc cgggggcggt gccccgcggt gcgggggggg ctgcgagggg    1260
aacaaaggct gcgtgcgggg tgtgtgcgtg ggggggtgag caggggggtgt gggcgcgtcg    1320
```

```
gtcgggctgc aaccccccct gcaccccct ccccgagttg ctgagcacgg cccggcttcg    1380
ggtgcgggc tccgtacggg gcgtggcgcg gggctcgccg tgccgggcgg ggggtggcgg    1440
caggtggggg tgccgggcgg ggcggggccg cctcgggccg gggagggctc gggggagggg   1500
cgcggcggcc cccggagcgc cggcggctgt cgaggcgcgg cgagccgcag ccattgcctt   1560
ttatggtaat cgtgcgagag ggcgcaggga cttcctttgt cccaaatctg tgcggagccg   1620
aaatctggga ggcgccgccg caccccctct agcgggcgcg gggcgaagcg gtgcggcgcc   1680
ggcaggaagg aaatgggcgg ggagggcctt cgtgcgtcgc cgcgccgccg tccccttctc   1740
cctctccagc ctcggggctg tccgcggggg gacggctgcc ttcgggggg acggggcagg    1800
gcggggttcg gcttctggcg tgtgaccggc ggctctagag cctctgctaa ccatgttcat   1860
gccttcttct ttttcctaca gctcctgggc aacgtgctgg ttattgtgct gtctcatcat   1920
tttggcaaag aattcgccac catgtacaag atgcagctgc tgagctgtat cgccctgacc   1980
ctggtgctgg tggccaactc tgaagtgcag ctggtggaaa gcggcggagg cctggtgcag   2040
cctggcggat ctctgagact gagctgtgcc gccagcggct tcaccttcag ccggtacagc   2100
atgagctggg tgcgccaggc ccctggcaaa ggactggaac tggtggccca gatcaacagc   2160
gtgggcaaca gcacctacta ccccgacacc gtgaagggcc ggttcaccat cagcagagac   2220
aacgccaaga acaccctgta cctgcagatg aacagcctgc gggccgagga caccgccgtg   2280
tactattgtg ccagcggcga ctattggggc cagggcacac tcgtgacagt gtctggcgga   2340
ggcggatctg ggggcggagg atcaggcggg ggaggatctg atgtcgtgat gacccagagc   2400
cccctgagcc tgcctgtgac actgggacag cctgccagca tcagctgcag aagcagccag   2460
agcctgatct acagcgacgg caacgcctac ctgcactggt ttctgcagaa acccggccag   2520
tcccccagac tgctgatcta taaggtgtcc aaccggttca gcggcgtgcc cgacagattt   2580
tctggcagcg gctccggcac cgacttcacc ctgaagatca gccgggtgga agccgaggac   2640
gtgggcgtgt actactgcag ccagtccacc cacgtgccct ggacatttgg acagggcacc   2700
aaggtggaaa tcaagcacca ccaccatcac cactgatgag gtacctctag agtcgacccg   2760
ggcggcctcg aggacggggt gaactacgcc tgaggatccg atcttttttcc ctctgccaaa   2820
aattatgggg acatcatgaa gccccttgag catctgactt ctggctaata aaggaaattt   2880
attttcattg caatagtgtg ttggaatttt ttgtgtctct cactcggaag caattcgttg   2940
atctgaattt cgaccaccca taatacccat taccctggta gataagtagc atggcgggtt   3000
aatcattaac tacaaggaac ccctagtgat ggagttggcc actccctctc tgcgcgctcg   3060
ctcgctcact gaggccgggc gaccaaaggt cgcccgacgc ccgggctttg cccgggcggc   3120
ctcagtgagc gagcgagcgc gcag                                         3144
```

INTRATHECAL ADMINISTRATION OF ADENO-ASSOCIATED-VIRAL VECTORS FOR GENE THERAPY

INCORPORATION-BY-REFERENCE OF MATERIAL SUBMITTED IN ELECTRONIC FORM

Applicant hereby incorporates by reference the Sequence Listing material filed herewith.

BACKGROUND OF THE INVENTION

Biomedical and pharmaceutical researchers have worked to devise new and more effective therapeutics to treat diseases affecting the central nervous system. However, the biology of the central nervous system itself, including the effectiveness of the blood-brain barrier in protecting the brain, poses a profound challenge to drug delivery. This leads to a lack of available treatment for many central nervous system diseases, such as stroke, neurodegenerative disorders, and brain tumors.

Neurodegeneration is the umbrella term for the progressive loss of structure or function of neurons, including death of neurons. Many neurodegenerative diseases, including amyotrophic lateral sclerosis (ALS), Parkinson's, Alzheimer's, and Huntington's occur as a result of neurodegenerative processes. A variety of therapies have been described for treatment of such neurodegenerative diseases, including monoclonal antibody therapy.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., J Virol. 45: 555-564 (1983) as corrected by Ruffing E T ah, J Gen Virol, 75: 3385-3392 (1994). Cis-acting sequences directing viral DNA replication (rep), encapsulation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and pi 9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka. Current Topics in Microbiology and Immunology, 158; 97-129 (1992). The coding sequences of the AAV genome can be provided in trans, making it possible to generate AAV vectors carrying a gene of interest rather than the endogenous viral genes. These AAV vectors are capable of gene transfer in vivo. Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV1. AAV9 is described in U.S. Pat. No. 7,198,951 and in Gao et al, J. Virol, 78: 6381-6388 (2004).

Intrathecal administration of an AAV vector carrying a single chain secretable ScFv antibody to target SOD1 has been described as a potential therapeutic approach for ALS. See, e.g., P Patel et al, Molecular Therapy (2014): 22, 3, 498-510.

What are needed are other methods for delivering immunoglobulin constructs, including without limitation, full-length antibodies, to the central nervous system.

SUMMARY OF THE INVENTION

A composition is provided which comprises an AAV vector formulated for intrathecal delivery to the central nervous system, wherein said composition comprises at least one expression cassette which contains sequences encoding an immunoglobulin product for delivery to the CNS operably linked to expression control sequences therefor and a pharmaceutically acceptable carrier and/or excipient. In one aspect, the composition is administered in the absence of chemical or physical disruption of the blood brain barrier. In one example, the immunoglobulin construct comprises an immunoglobulin modified to have decreased or no measurable affinity for neonatal Fc receptor (FcRn).

In one aspect, a composition is described which comprises an AAV vector formulated for intrathecal delivery for treatment of a condition of the central nervous system, wherein said composition comprises an AAV vector comprising an AAV capsid which targets a cell of the central nervous system, the capsid having packaged therein at least one AAV inverted terminal repeat sequence and sequences encoding an immunoglobulin construct operably linked to expression control sequences therefor, the composition further comprising a pharmaceutically acceptable carrier and/or excipient. Suitably, the encoded immunoglobulin is mutated or engineered to have decreased or no measurable affinity for neonatal Fc receptor (FcRn).

Use of a composition comprising at least one AAV vector stock encoding the immunoglobulin construct useful in treatment of a neurological disorder, and/or an infectious disease of the central nervous system, is provided herein.

In another aspect, a method for treatment of Alzheimer's Disease is provided which involves intrathecal delivery of an AAV vector composition as described herein, in which at least one AAV vector stock expresses an immunoglobulin specific for a Aβ, beta secretase, and/or the tau protein, to subject in need thereof.

In yet another aspect, a method for treatment of ALS is provided which involves intrathecal delivery of an AAV vector composition as described herein, in which at least one AAV vector stock expresses an immunoglobulin specific for ALS enzyme superoxide dismutase 1 (SOD1) and variants thereof, provided the anti-SOD1 antibody is other than an ScFv fragment, a Derlin-1-binding region, and/or an antibody construct against neurite outgrowth inhibitor.

In still another embodiment, a method for treatment of Parkinson's Disease or related synucleinopathies is provide which involves intrathecal delivery of an AAV vector composition as provided herein, in which at least one AAV vector stock encodes one or more leucine-rich repeat kinase 2 antibody, dardarin (LRRK2) antibody, alpha-synuclein antibody, and/or DJ-1 (PARK7) antibody.

In yet a further aspect, a method for treatment of multiple sclerosis is provided herein which involves intrathecal delivery of an AAV vector composition as provided herein, in which composition at least one vector stock encodes an immunoglobulin directed against one or more of an a4-integrin, CD20, CD25, IL12, p40+IL23p40, LINGO-1, CD40, and rHIgM22, CD52, IL17, CD19, and/or SEMA4D.

In another aspect, a method for treatment of infectious disease of the central nervous system is provided which involves intrathecal delivery of an AAV vector composition as provided herein, in which composition at least one vector stock encodes an immunoglobulin directed against the pathogen which causes said infectious disease. Examples, without limitation, include one or more immunoglobulins directed against one or more of *Mycobacterium tuberculosis* (tuberculosis), *Neisseria meningitides* (meningitis), *Streptococcus pneumonia, Listeria monocytogens* (listeriosis), *Borrelia burdorferia* (lyme disease), human deficiency virus (acquired immunodeficiency syndrome), a herpes family viruses, varicella zoster virus, Epstein-Barr virus (EBV), cytomegalovirus, and/or JC virus. Other examples of immunoglobulin targets are provided elsewhere in this application and are incorporated by reference herein.

In one aspect a method is provided for treatment of prion related diseases which comprises intrathecal delivery of an AAV vector composition, in which at least one vector stock encodes an immunoglobulin directed one or more of major prion protein, or PrPSc.

Still other aspects and advantages of the invention will be readily apparent from the following detailed description of the invention.

DETAILED DESCRIPTION OF THE INVENTION

Figure 1A:
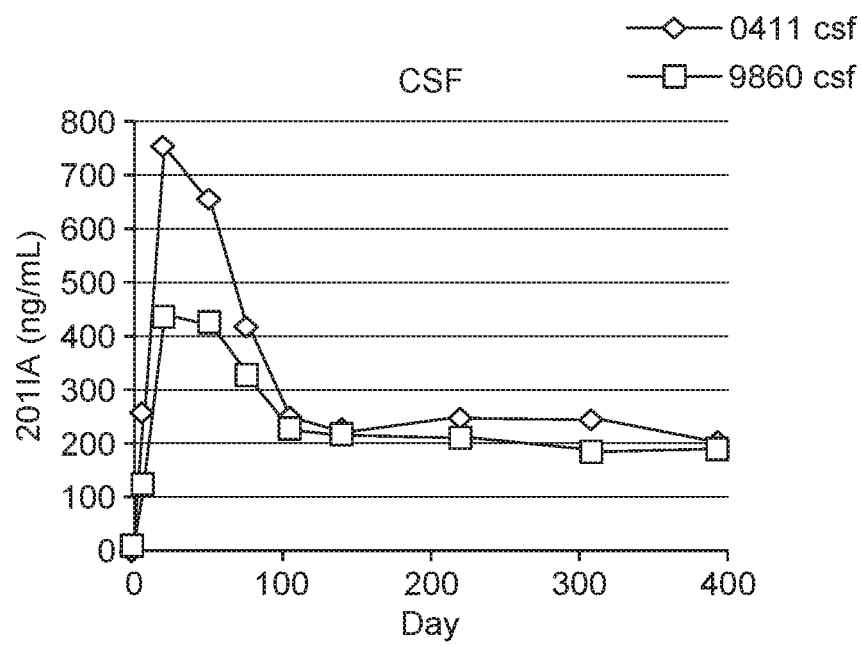
FIG. 1A is a graph which shows concentration of a rhesus macaque derived immunoadhesin (201IA) in cerebrospinal fluid (CSF) for two animals receiving an AAV9 vector expressing the immunoadhesin under a chicken f-actin (CB) promoter delivered intrathecally by suboccipital puncture. CSF was collected periodically following vector administration, with 400 days being the last collection time point shown. The scale for CSF is up to 800 ng/mL.
Figure 1B:
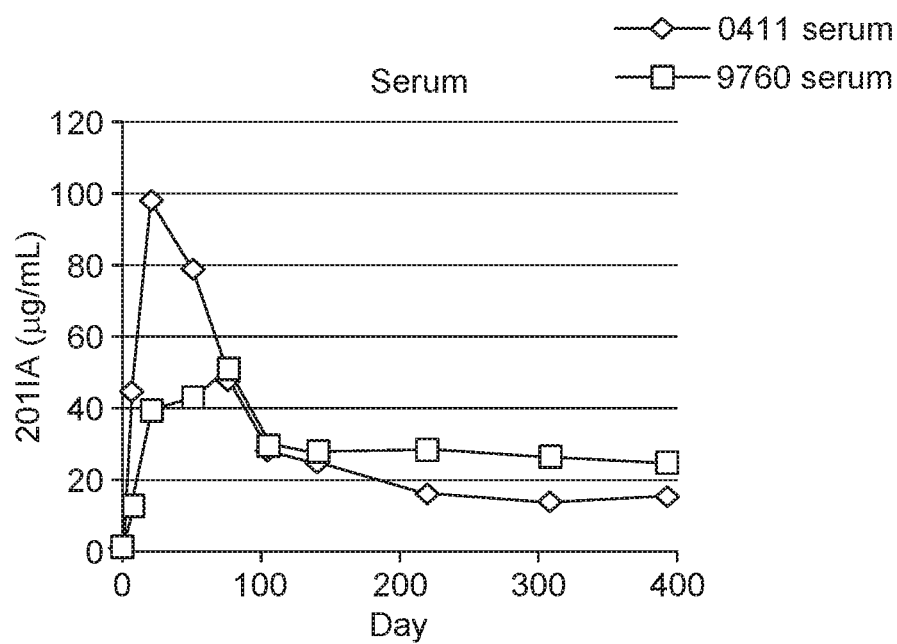
FIG. 1B is a graph which shows concentration of a rhesus macaque derived immunoadhesin (201IA) in serum for two animals receiving an AAV9 vector expressing the immunoadhesin under a chicken f-actin (CB) promoter delivered intrathecally by suboccipital puncture. Serum was collected periodically following vector administration, with 400 days being the last collection time point shown. The concentration scale for serum is up to 120 µg/mL.

The compositions and regimens described herein are useful for delivery of immunoglobulin constructs to the central nervous system. Compositions described herein comprising AAV having immunoglobulin constructs for intrathecal delivery to the central nervous system (CNS).

As used herein, an immunoglobulin construct (including antibody or antibody fragment as defined herein) encodes a polypeptide-based moiety which binds to a cell-surface antigen or receptor located within the central nervous system. Such a receptor may be located on a bacteria, virus, fungus, or other pathogen which has infected the central nervous system, and/or proteins associated with a disorder of the central nervous system and/or such a pathogen, e.g., secreted proteins and/or protein aggregates.

The term "immunoglobulin" is used herein to include antibodies, functional fragments thereof, and immunoadhesins. Antibodies may exist in a variety of forms including, for example, polyclonal antibodies, monoclonal antibodies, camelid single domain antibodies, intracellular antibodies ("intrabodies"), recombinant antibodies, multispecific antibody, antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, and the like. "Antibody fragment" refers to at least a portion of the variable region of the immunoglobulin that binds to its target, e.g., the cell-surface antigen or receptor.

In one embodiment, a composition as described herein provides for AAV-mediated delivery of an immunoglobulin which includes a fragment crystallizable region (Fc portion), including, such as is present in a full-length antibody, a bispecific antibody, an immunoadhesin [containing the immunoglobulin constant domains, and typically also the hinge and Fc regions], a monoclonal antibody, a heavy chain camelid or shark immunoglobulins Use of AAV to deliver full-length antibodies and two antibody combinations have been described, e.g., in "Compositions Comprising AAV Expressing Dual Antibody Constructs and Uses Thereof", International Application No. PCT/US15/30533, filed May 13, 2015, "Methods and Compositions for Treating Metastatic Breast Cancer and Other Cancers in the Brain", International Application No. PCT/US15/27491, filed Apr. 24, 2015, and which are incorporated by reference herein. Optionally, a composition may contain two or more different AAV-immunoglobulin constructs as described herein.

In another embodiment, a composition as described herein provides for AAV-mediated delivery of an immunoglobulin which excludes an Fc portion, e.g., a Fab (fragment antigen-binding fragment, typically formed by papain digestion of Ab), a F(ab')$_2$ fragment (containing two antigen binding fragments, typically formed by pepsin digestion of Ab), a Fab' fragment (typically formed by reduction of F(ab')$_2$), Fab'-SH, a F(ab)$_3$ (a trispecific antibody fragment), an Fv (immunoglobulin containing only the two variable domains), a single domain antibody (sdAb or V$_H$H nanobody), e.g., a camelid or shark antibody, or an scFv construct. Such a composition may include two or more different AAVscFv constructs.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

As used herein, an "expression cassette" refers to a nucleic acid molecule which comprises an immunoglobulin gene(s) (e.g., an immunoglobulin variable region, an immunoglobulin constant region, a full-length light chain, a full-length heavy chain or another fragment of an immunoglobulin construct), promoter, and may include other regulatory sequences therefor, which cassette may be delivered via a genetic element (e.g., a plasmid) to a packaging host cell and packaged into the capsid of a viral vector (e.g., a viral particle). Typically, such an expression cassette for generating a viral vector contains the immunoglobulin sequences described herein flanked by packaging signals of the viral genome and other expression control sequences such as those described herein.

As used herein, a "vector stock" or an "AAV vector stock" refers to population of genome copies of an AAV viral particle having packaged therein a non-AAV sequence which encodes an immunoglobulin(s) as defined herein. Suitably, a vector stock includes a sufficient number of genome copies (GC) of the recombinant AAV vector to achieve a desired physiologic effect. Where a desired physiologic effect is achieved, the amount of vector stock in a composition, dose, or regimen, may be referred to as an "effective amount" of rAAV vector or vector stock.

Unless otherwise specified, the "central nervous system" refers to the spinal cord and brain and contrasts with the "peripheral nervous system" which excludes the spinal cord and brain. There are different cell types within the central nervous system, including neuronal cells and glial cells. The glia in mature systems include astrocytes, oligodendrocytes, and microglial cells. The AAV capsids for the vectors used in the present invention are preferably selected from among those which will transduce and/or express in at least one of these cell types of the central nervous system.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipitallintracisternal, and/or C1-2 puncture. For example, material may be introduced for diffusion throughout the subarachnoid space by means of lumbar puncture. In another example, injection may be into the cisterna *magna*.

As used herein, the terms "intracisternal delivery" or "intracisternal administration" refer to a route of administration for drugs directly into the cerebrospinal fluid of the cisterna *magna* cerebellomedularis, more specifically via a suboccipital puncture or by direct injection into the cisterna *magna* or via permanently positioned tube.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

For expression from an AAV vector, nucleic acid constructs which encode immunoglobulins useful in treatment of one or more neurodegenerative disorders may be engineered or selected for delivery via an AAV composition of the invention. Such disorders may include, without limitation, transmissible spongiform encephalopathies (e.g., Creutzfeld-Jacob disease), Parkinson's disease, amyotropic lateral sclerosis (ALS), multiple sclerosis, Alzheimer's Disease, Huntington disease, Canavan's disease, traumatic brain injury, spinal cord injury (ATI335, anti-nogol by Novartis), migraine (ALD403 by Alder Biopharmaceuticals; LY2951742 by Eli; RN307 by Labrys Biologics), lysosomal storage diseases, stroke, and infectious disease affecting the central nervous system.

Still other nucleic acids may encode an immunoglobulin which is directed to leucine rich repeat and immunoglobulin-like domain-containing protein 1 (LINGO-1), which is a functional component of the Nogo receptor and which is associated with essential tremors in patients which multiple sclerosis, Parkinson's Disease or essential tremor. One such commercially available antibody is ocrelizumab (Biogen, BIIB033). See, e.g., U.S. Pat. No. 8,425,910.

In one embodiment, the nucleic acid constructs encode immunoglobulin constructs useful for patients with ALS. Examples of suitable antibodies include antibodies against the ALS enzyme superoxide dismutase 1 (SOD1) and variants thereof (e.g., ALS variant G93A, C4F6 SOD1 antibody); MS785, which directed to Derlin-1-binding region); antibodies against neurite outgrowth inhibitor (NOGO-A or Reticulon 4), e.g., GSK1223249, ozanezumab (humanized, GSK, also described as useful for multiple sclerosis).

Nucleic acid sequences may be designed or selected which encode immunoglobulins useful in patients having Alzheimer's Disease. Such antibody constructs include, e.g., adumanucab (Biogen), Bapineuzumab (Elan; a humanised mAb directed at the amino terminus of A$\beta$); Solanezumab Eli Lilly, a humanized mAb against the central part of soluble A$\beta$); Gantenerumab (Chugai and Hoffmann-La Roche, is a full human mAb directed against both the amino terminus and central portions of A$\beta$); Crenezumab (Genentech, a humanized mAb that acts on monomeric and conformational epitopes, including oligomeric and protofibrillar forms of A$\beta$; BAN2401 (Esai Co., Ltd, a humanized immunoglobulin G1 (IgG1) mAb that selectively binds to A$\beta$ protofibrils and is thought to either enhance clearance of A$\beta$ protofibrils and/or to neutralize their toxic effects on neurons in the brain); GSK 933776 (a humanised IgG1 monoclonal antibody directed against the amino terminus of A$\beta$); AAB-001, AAB-002, AAB-003 (Fc-engineered bapineuzumab); SAR228810 (a humanized mAb directed against protofibrils and low molecular weight A$\beta$); BIIB037/BART (a full human IgG1 against insoluble fibrillar human A$\beta$, Biogen Idec), an anti-A$\beta$ antibody such m266, tg2576 (relative specificity for A$\beta$ oligomers) [Brody and Holtzman, Annu Rev Neurosci, 2008; 31: 175-193]. Other antibodies may be targeted to beta-amyloid proteins, A$\beta$, beta secretase and/or the tau protein.

Illustrated in the examples herein are three anti-A$\beta$ scFv constructs designed to eliminate the Fc region of full-length anti-amyloid beta (A$\beta$). These constructs were designed to reduce the risk of amyloid related imaging abnormalities and/or to limit the exposure of vessels to high monoclonal antibody concentrations. In one embodiment, an illustrative scFV binds fibrillar 0-amyloid. See, e.g., the scFV having the amino acid sequence of SEQ ID NO: 8, in which the heavy chain variable region has the sequence of amino acids 21 to 143 and the light chain variable region has the sequence of amino acids 159 to 265. Also encompassed are variants of this scFV. For example, with reference to SEQ ID NO: 8, a different signal sequence (amino acids 1-20), a different linker may be substituted for the Gly-Ser linker (amino acids 144 to 158), or the His tag may be removed (amino acids 266 to 271). Provided herein are nucleic acid sequences encoding the scFV amino acid sequences described herein. See, e.g., SEQ ID NO: 7.

In another embodiment, an illustrative scFV is directed against the oligomeric, soluble, and fibrillary 0-amyloid. See. e.g., the amino acid sequence of SEQ ID NO: 10, having the heavy chain variable region of aa 21 to 131 and the light chain variable region of aa 147 to 258. Also encompassed are variants of this scFV. For example, with reference to SEQ ID NO: 10, a different signal sequence (amino acids 1-20), a different linker may be substituted for the Gly-Ser linker (amino acids 132 to 146), or the His tag may be removed (amino acids 259-264). Provided herein are nucleic acid sequences encoding the scFV amino acid sequences described herein. See, e.g., SEQ ID NO: 9.

In still another embodiment, an illustrative scFV is directed against soluble β-amyloid. See, e.g., the amino acid sequence of SEQ ID NO: 12, having the heavy chain variable region of aa 21 to 131 and the light chain variable region of as 147 to 258. Also encompassed are variants of this scFV. For example, with reference to SEQ ID NO: 12, a different signal sequence (amino acids 1-20), a different linker may be substituted for the Gly-Ser linker (amino acids 132 to 146), or the His tag may be removed (amino acids 259-264). Provided herein are nucleic acid sequences encoding the scFV amino acid sequences described herein. See, e.g., SEQ ID NO: 11.

In still other embodiments, an anti-f3-amyloid antibody is derived from an IgG4 monoclonal antibodies to target β-amyloid in order to minimize effector functions, or construct other than an scFv which lacks an Fc region is selected in order to avoid amyloid related imaging abnormality (ARIA) and inflammatory response. In certain of these embodiments, the heavy chain variable region and/or the light chain variable region of one or more of the scFv constructs is used in another suitable immunoglobulin construct as provided herein. These scFV and other engineered immunoglobulins may reduce the half-life of the immunoglobulin in the serum, as compared to immunoglobulins containing Fc regions. Reducing the serum concentration of anti-amyloid molecules may further reduce the risk of ARIA, as extremely high levels of anti-amyloid antibodies in serum may destabilize cerebral vessels with a high burden of amyloid plaques, causing vascular permeability.

Nucleic acids encoding other immunoglobulin constructs for treatment of patients with Parkinson's disease may be engineered or designed to express constructs, including, e.g., leucine-rich repeat kinase 2, dardarin (LRRK2) antibodies; anti-synuclein and alpha-synuclein antibodies and DJ-1 (PARK7) antibodies. Other antibodies may include, PRX002 (Prothena and Roche) Parkinson's disease and related synucleinopathies. These antibodies, particularly anti-synuclein antibodies may also be useful in treatment of one or more lysosomal storage disease.

One may engineer or select nucleic acid constructs encoding an immunoglobulin construct for treating multiple sclerosis. Such immunoglobulins may include or be derived from antibodies such as natalizumab (a humanized anti-a4-ingrin, iNATA, Tysabri, Biogen Idec and Elan Pharmaceuticals), which was approved in 2006, alemtuzumab (Campath-1H, a humanized anti-CD52), rituximab (rituzin, a chimeric anti-CD20), daclizumab (Zenepax, a humanized anti-CD25), ocrelizumab (humanized, anti-CD20, Roche), ustekinumab (CNTO-1275, a human anti-IL12 p40+ IL23p40); anti-LINGO-1, and ch5D12 (a chimeric anti-CD40), and rHIgM22 (a remyelinated monoclonal antibody; Acorda and the Mayo Foundation for Medical Education and Research). Still other anti-a4-integrin antibodies, anti-CD20 antibodies, anti-CD52 antibodies, anti-IL17, anti-CD19, anti-SEMA4D, and anti-CD40 antibodies may be delivered via the AAV vectors as described herein.

AAV-mediated delivery of antibodies against various infections of the central nervous system is also contemplated by the present invention. Such infectious diseases may include fungal diseases such as cryptoccocal meningitis, brain abscess, spinal epidural infection caused by, e.g., *Cryptococcus neoformans*, *Coccidioides immitis*, order Mucorales, *Aspergillus* spp, and *Candida* spp; protozoal, such as toxoplasmosis, malaria, and primary amoebic meningoencepthalitis, caused by agents such as, e.g., *Toxoplasma gondii*, *Taenia solium*, *Plasmodium falciparus*, *Spirometra mansonoides* (sparaganoisis), *Echinococcus* spp (causing neuro hydatosis), and cerebral amoebiasis; bacterial, such as, e.g., tuberculosis, leprosy, neurosyphilis, bacterial meningitis, lyme disease (*Borrelia burgdorferi*), Rocky Mountain spotted fever (*Rickettsia rickettsia*), CNS nocardiosis (*Nocardia* spp), CNS tuberculosis (*Mycobacterium tuberculosis*), CNS listeriosis (*Listeria monocytogenes*), brain abscess, and neuroborreliosis; viral infections, such as, e.g., viral meningitis, Eastern equine encephalitis (EEE), St Louis encepthalitis, West Nile virus and/or encephalitis, rabies, California encephalitis virus, La Crosse encepthalitis, measles encephalitis, poliomyelitis, which may be caused by, e.g., herpes family viruses (HSV), HSV-1, HSV-2 (neonatal herpes simplex encephalitis), varicella zoster virus (VZV), Bickerstaff encephalitis, Epstein-Barr virus (EBV), cytomegalovirus (CMV, such as TCN-202 is in development by Theraclone Sciences), human herpesvirus 6 (HHV-6), B virus (herpesvirus *simiae*), Flavivirus encephalitis, Japanese encephalitis, Murray valley fever, JC virus (progressive multifocal leukoencephalopathy), Nipah Virus (NiV), measles (subacute sclerosing panencephalitis); and other infections, such as, e.g., subactuate sclerosing panencephalitis, progressive multifocal leukoencephalopathy; human immunodeficiency virus (acquired immunodeficiency syndrome (AIDS)); *Streptococcus pyogenes* and other β-hemolytic *Streptococcus* (e.g., Pediatric Autoimmune Neuropsychiatric Disorders Associated with Streptococcal Infection, PANDAS) and/or Syndenham's chorea, and Guillain-Barre syndrome, and prions.

Examples of suitable antibody constructs may include those described, e.g., in WO 2007/012924A2, Jan. 29, 2015, which is incorporated by reference herein.

For example, other nucleic acid sequences may encode anti-prion immunoglobulin constructs. Such immunoglobulins may be directed against major prior protein (PrP, for prion protein or protease-resistant protein, also known as CD230 (cluster of differentiation 230). The amino acid sequence of PrP is provided, e.g., world wide web at: ncbi.nlm.nih.gov/protein/NP_000302, incorporated by reference herein. The protein can exist in multiple isoforms, the normal PrP$^C$, the disease-causing PrP$^{Sc}$, and an isoform located in mitochondria. The misfolded version PrP$^{Sc}$ is associated with a variety of cognitive disorders and neurodegenerative diseases such as Creutzfeldt-Jakob disease, bovine spongiform encephalopathy, Gerstmann-Sträussler-Scheinker syndrome, fatal familial insomnia, and kuru.

Once the target and immunoglobulin are selected, the coding sequences for the selected immunoglobulin (e.g., heavy and/or light chain(s)) may be obtained and/or synthesized. Methods for sequencing a protein, peptide, or polypeptide (e.g., as an immunoglobulin) are known to those of skill in the art. Once the sequence of a protein is known, there are web-based and commercially available computer programs, as well as service based companies which back translate the amino acids sequences to nucleic acid coding sequences. See, e.g., backtranseq by EMBOSS, (www.ebi-.ac.uk/Tools/st/); Gene Infinity www.geneinfinity.org/sms/sms_backtranslation.html); ExPasy (www.expasy.org/tools/). In one embodiment, the RNA and/or cDNA coding sequences are designed for optimal expression in human cells.

Codon-optimized coding regions can be designed by various different methods. This optimization may be performed using methods which are available on-line (e.g., GeneArt), published methods, or a company which provides codon optimizing services, e.g., DNA2.0 (Menlo Park, Calif.). One codon optimizing algorithm is described, e.g., in US International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The immunoglobulin genes described herein may be used to express the "wild-type", a published or commercially available, or other known constant immunoglobulin domains or can be engineered to decrease affinity for, or ablate, binding to the Fc binding site present on immunoglobulins. There are several different types of Fc receptors, which are classified based on the type of antibody that they recognize. As used herein, "FcRn" refers to the neonatal Fc receptor that binds IgG. It is similar in structure to MHC class I protein. In humans, it is encoded by the FCGRT gene. The Fc receptor is located on various cells types, including, e.g., the epithelial cells of the blood brain barrier. The term "FcRn binding domain" as used herein refers to a protein domain that directly or indirectly binds to the FcRn. The FcRn may be a mammalian FcRn. In further embodiments, the FcRn is a human FcRn. An FcRn binding domain binding directly to an FcRn is an antibody Fc region. Meanwhile, regions capable of binding to a polypeptide such as albumin or IgG, which has human FcRn-binding activity, can indirectly bind to human FcRn via albumin, IgG, or such. Thus, such a human FcRn-binding region may be a region that binds to a polypeptide having human FcRn-binding activity. The term "Fc region" as used herein refers to an FcRn-binding domain that directly binds to FcRn, a mammalian FcRn, or a human FcRn. In particular, an Fc region is an Fc region of an antibody. The Fc region may be a mammalian Fc region or more particularly a human Fc region. In particular, the Fc region may be located within the second and third constant domain of a human immunoglobulin (CH2 and CH3). Further, the Fc region may be the hinge of CH2 and CH3. In one embodiment, the immunoglobulin construct is an IgG. In a further embodiment, the Fc region is an Fc region of human IgG1. Other Ig isotypes can be used as well.

Methods and computer programs for preparing such alignments are available and well known to those of skill in the art. Substitutions may also be written as (amino acid identified by single letter code)-position #-(amino acid identified by single letter code) whereby the first amino acid is the substituted amino acid and the second amino acid is the substituting amino acid at the specified position. The terms "substitution" and "substitution of an amino acid" and "amino acid substitution" as used herein refer to a replacement of an amino acid in an amino acid sequence with another one, wherein the latter is different from the replaced amino acid. Methods for replacing an amino acid are well known to the skilled in the art and include, but are not limited to, mutations of the nucleotide sequence encoding the amino acid sequence. Methods of making amino acid substitutions in IgG are described, e.g., for WO 2013/046704, which is incorporated by reference for its discussion of amino acid modification techniques, although this document describes increasing FcRn affinity, rather than decreasing or ablating binding affinity as described herein.

The term "amino acid substitution" and its synonyms described above are intended to encompass modification of an amino acid sequence by replacement of an amino acid with another, substituting amino acid. The substitution may be a conservative substitution. The term conservative, in referring to two amino acids, is intended to mean that the amino acids share a common property recognized by one of skill in the art. The term non-conservative, in referring to two amino acids, is intended to mean that the amino acids which have differences in at least one property recognized by one of skill in the art. For example, such properties may include amino acids having hydrophobic nonacidic side chains, amino acids having hydrophobic side chains (which may be further differentiated as acidic or nonacidic), amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Thus, a conservative amino acid substitution may involve changing a first amino acid having a hydrophobic side chain with a different amino acid having a hydrophobic side chain; whereas a non-conservative amino acid substitution may involve changing a first amino acid with an acidic hydrophobic side chain with a different amino acid having a different side chain, e.g., a basic hydrophobic side chain or a hydrophilic side chain. Still other conservative or non-conservative changes change be determined by one of skill in the art.

In still other embodiments, the substitution at a given position will be to an amino acid, or one of a group of amino acids, that will be apparent to one of skill in the art in order to accomplish an objective identified herein.

In one embodiment, an immunoglobulin construct as defined herein is engineered so that the native sequence located on the conserved region of the immunoglobulin Fc region is ablated to eliminate binding to the FcRn and to minimize or eliminate transport of the proteinaceous immunoglobulin constructs across the blood brain barrier (out of the CNS area) and into the systemic circulation. In one example, this may be accomplished by altering one or more amino acids of the FcRn-binding domain, e.g., by modification of the codon for the selected amino acid(s). See. e.g., U.S. Pat. No. 8,618,252 B2, Additionally or alternatively, immunoglobulin constructs (e.g., Fc variants) are engineered to have enhanced effector function are selected. See. e.g., T. Matsushita, Korean J Hematol, 2011 September; 46(3): 148-150; U.S. Pat. No. 6,946,292.

The heavy chain amino acid numbering used herein to identify the location of the mutants is based on the EU numbering system [IMGT unique numbering, Edelman, G. M. et al., Proc. Natl. Acad. USA, 63, 78-85 (1969); (www.imgt.org/-IMGTScientificChart/)] and refer to positions in an FcRn-binding domain, in particular in an Fc region. In a similar fashion, substitutions are indicated as for example "EU387R" or "EU440E", wherein the number given after "EU" indicates the position of the substitution according the EU numbering, and the letter after the number is the substituted amino acid given in the one letter code. Other numbering systems include, e.g., Kabat, E. A., T. T. Wu, H. M. Perry, K. S. Gottesman, C. Foeler. (1991) Sequences of Proteins of Immunological Interest. No. 91-3242 U. S. Public Health Services, National Institutes of Health, Bethesda).

The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter.

In certain embodiments, the expression cassette described herein contains at least one internal ribosome binding site, i.e., an IRES, located between the coding regions of the heavy and light chains. Alternatively the heavy and light chain may be separated by a furin-2a self-cleaving peptide linker [see. e.g., Radcliffe and Mitrophanous, Gene Therapy (2004), 11, 1673-1674. The expression cassette may contain at least one enhancer, i.e., CMV enhancer. Still other enhancer elements may include. e.g., an apolipoprotein enhancer, a zebrafish enhancer, a GFAP enhancer element, and brain specific enhancers such as described in WO 2013/1555222, woodchuck post hepatitis post-transcriptional regulatory element. Additionally, or alternatively, other, e.g., the hybrid human cytomegalovirus (HCMV)-immediate early (IE)-PDGR promoter or other promoter—enhancer elements may be selected. To enhance expression the other elements can be introns (like Promega™ intron or chimeric chicken globin-human immunoglobulin intron).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See. e.g., J. D. Thomson et al, *Nucl. Acids. Res.*, "A comprehensive comparison of multiple sequence alignments", 27(13):2682-2690 (1999).

In another embodiment, a modified immunoglobulin having its affinity for FcRn ablated and retaining physiologically effective activity is provided. One or more amino acid modifications may be selected to ablate functional binding to FcRn. In one embodiment, the mutation lowers the binding affinity of the immunoglobulin for FcRn to less than 10% of the native protein. Suitably, the immunoglobulins with these mutations bind substantially normally to all other Fc receptors. Once the amino acid sequence is selected, the nucleic acid sequences can be designed and/or the previously described sequences may be engineered as described above. These modifications are made by engineering the nucleic acid coding region using site directed mutagenesis or other genetic engineering techniques which are known to those of skill in the art.

In one embodiment, the immunoglobulin genes described herein are engineered into a genetic element (e.g., a plasmid) useful for generating AAV vectors which transfer the immunoglobulin construct sequences carried thereon. The examples herein and SEQ ID NO: 13, 14 and 15, respectively illustrate AAV vector genomes with three different scFV constructs directed to Aβ targets. The selected vector may be delivered to an AAV packaging cell by any suitable method, including transfection, electroporation, liposome delivery, membrane fusion techniques, high velocity DNA-coated pellets, viral infection and protoplast fusion. Stable packaging cells can also be made. The methods used to make such constructs are known to those with skill in nucleic acid manipulation and include genetic engineering, recombinant engineering, and synthetic techniques. See. e.g., Molecular Cloning: A Laboratory Manual, ed. Green and Sambrook, Cold Spring Harbor Press, Cold Spring Harbor, N.Y. (2012).

AAV Vectors

An AAV vector as described herein can comprise one or more nucleic acid sequences, each of which encodes one or more of the heavy and/or light chain polypeptides, or other polypeptides, of an immunoglobulin construct. Suitably, a composition contains one or more AAV vectors which contain nucleic acid sequences encoding all of the polypeptides which form an immunoglobulin construct in vivo. For example, a full-length antibody consists of four polypeptides: two copies of a heavy (H) chain polypeptide and two copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. In this respect, an AAV vector as described herein can comprise a single nucleic acid sequence that encodes the heavy chain polypeptides (e.g., constant variable) and the light chain polypeptides of an immunoglobulin construct. Alternatively, the AAV vector can comprise a first expression cassette that encodes at least one heavy chain constant polypeptides and at least one heavy chain variable polypeptide, and a second expression cassettes that encodes constant and variable light chain polypeptides of an immunoglobulin construct. In yet another embodiment, the AAV vector can comprise a first expression cassette encoding a first heavy chain polypeptide, a second expression cassette encoding a second heavy chain polypeptide, and a third expression cassette encoding a light chain polypeptide is shared by the two heavy chains. In another embodiment, an AAV vector may express 1, 2, 3 or 4 scFv open reading frames (ORFs), each of which may be same or different.

Typically, an expression cassette for an AAV vector comprises an AAV 5' inverted terminal repeat (ITR), the immunoglobulin construct coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

Where a pseudotyped AAV is to be produced, the ITRs in the expression are selected from a source which differs from the AAV source of the capsid. For example, AAV2 ITRs may be selected for use with an AAV capsid having a particular efficiency for targeting CNS or tissues or cells within the CNS. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

The abbreviation "scAAV" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See. e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The expression cassette typically contains a promoter sequence as part of the expression control sequences, e.g., located between the selected 5' ITR sequence and the immunoglobulin construct coding sequence. Tissue specific promoters, constitutive promoters, regulatable promoters [see. e.g., WO 2011/126808 and WO 2013/04943], or a promoter responsive to physiologic cues may be used may be utilized in the vectors described herein. In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product.

These control sequences are "operably linked" to the immunoglobulin construct gene sequences. As used herein, the term "operably linked" refers to both expression control sequences that are contiguous with the gene of interest and expression control sequences that act in trans or at a distance to control the gene of interest.

In one embodiment, a self-complementary AAV is provided. This viral vector may contain a Δ5' ITR and an AAV 3' ITR. In another embodiment, a single-stranded AAV viral vector is provided. Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In one system, a producer cell line is transiently transfected with a construct that encodes the transgene flanked by ITRs and a construct (s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The available space for packaging may be conserved by combining more than one transcription unit into a single expression cassette, thus reducing the amount of required regulatory sequences. For example, a single promoter may direct expression of a single RNA that encodes two or three or more genes, and translation of the downstream genes are driven by IRES sequences. In another example, a single promoter may direct expression of an RNA that contains, in a single open reading frame (ORF), two or three or more genes separated from one another by sequences encoding a self-cleavage peptide (e.g., 2A) and/or a protease recognition site (e.g., furin). The ORF thus encodes a single polyprotein, which, either during or after translation, is cleaved into the individual proteins (such as, e.g., heavy chain and light chain). It should be noted, however, that although these IRES and polyprotein systems can be used to save AAV packaging space, they can only be used for expression of components that can be driven by the same promoter. In another alternative, the transgene capacity of AAV can be increased by providing AAV ITRs of two genomes that can anneal to form head to tail concatamers. In a further alternative, bidirectional promoters may be selected.

In the examples below, an AAV vector having an AAV9 capsid is described. As used herein, "AAV9 capsid" refers to the AAV9 having the amino acid sequence of GenBank accession: AAS99264, which is incorporated by reference herein. Some variation from this encoded sequence is encompassed by the present invention, which may include sequences having at least about 95%, at least about 97% or at least about 99% identity to the referenced amino acid sequence in GenBank accession:AAS99264 and U.S. Pat. No. 7,906,111 (also WO 2005/033321). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1. Generation of AAV9 vectors is described, e.g., in U.S. Pat. No. 7,906,111, which is incorporated herein by reference. However, other sources of AAV capsids and other viral elements may be selected, as may other immunoglobulin constructs and other vector elements. Methods of generating AAV vectors have been described extensively in the literature and patent documents, including, e.g., WO 2003/042397; WO 2005/033321, WO 2006/110689; U.S. Pat. No. 7,588,772 B2. The source of AAV capsids may be selected from an AAV which targets CNS, specific cells within the CNS, and/or specific antigens or receptors. Suitable AAV may include, e.g, AAV9 [U.S. Pat. No. 7,906,111; US 2011-0236353-A1], rh10 [WO 2003/042397] and/or hu37 [see, e.g., U.S. Pat. No. 7,906,111; US 2011-0236353-A1]. However, other AAV, including, e.g., AAV1, AAV2, AAV3, AAV4, AAV5, AAV6, AAV7, AAV8 [U.S. Pat. Nos. 7,790,449; 7,282,199] and others may be selected for preparing the AAV vectors described herein.

Uses and Regimens

Suitably, the composition of the invention are designed so that AAV vectors carry the nucleic acid expression cassettes encoding the immunoglobulin constructs and regulatory sequences which direct expression of the immunoglobulin thereof in the selected cell. Following administration of the vectors into the CNS, the vectors deliver the expression cassettes to the CNS and express the proteinaceous immunoglobulin constructs in vivo. The use of compositions described herein for a therapeutic purpose are described, as are uses of these compositions in various regimens, which may optionally involve delivery of one or more other active agents.

As stated above, a composition may contain a single type of AAV vector as described herein which contains the expression cassette for delivering the immunoglobulin construct in vivo. Alternatively, a composition may contain two or more different AAV vectors, each of which has packaged therein different expression cassettes. For example, the two or more different AAV may have different expression cassettes which express immunoglobulin polypeptides which assemble in vivo to form a single functional immunoglobulin construct. In another example, the two or more AAV may have different expression cassettes which express immunoglobulin polypeptides for different targets, e.g., two provide for two functional immunoglobulin constructs (e.g., a first immunoglobulin construct and a second immunoglobulin construct). In still another alternative, the two or more different AAV may express immunoglobulin constructs directed to the same target, wherein one of the immunoglobulin constructs has been modified to ablate FcRn binding and a second immunoglobulin construct which retains its ability or has enhanced ability to bind to FcRn. Such a composition may be useful to simultaneously provide antibodies with increased retention in the CNS and antibodies for systemic delivery of the immunoglobulin construct.

A regimen as described herein may comprise, in addition to one or more of the combinations described herein, further combination with one or more of a biological drug, a small molecule drug, or other therapy. A biological drug as described herein, is based on a peptide, polypeptide, protein, enzyme, nucleic acid molecule, vector (including viral vectors), or the like.

Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery. In one embodiment, intrathecal delivery encompasses an injection into the spinal canal, e.g., the subarachnoid space. However, other routes of delivery may be selected and the pharmaceutically acceptable carriers for the AAV compositions including, e.g., intracranial, intranasal, intracisternal, intracerebrospinal fluid delivery, among other suitable direct or systemic routes, i.e. Ommaya reservoir.

The compositions can be formulated to contain an amount of AAV that is in the range of about $1\times10^9$ genome copies (GC) to about $5\times10^{14}$ GC. In one example, the vector is about $3\times10^{13}$ GC, but other amounts such as about $1\times10^9$ GC, about $5\times10^9$ GC, about $1\times10^{10}$ GC, about $5\times10^{10}$ GC, about $1\times10^{11}$ GC, about $5\times10^{11}$ GC, about $1\times10^{12}$ GC, about $5\times10^{12}$ GC, or about $5\times10^{13}$ GC. Such compositions may contain a single AAV stock which expresses an immunoglobulin directed to a selected target. In another embodiment, such compositions may contain two AAV stock which co-express an immunoglobulin which assembles in the targeted host cell to form the desired immunoglobulin (e.g., a full-length antibody) against a selected target. In another embodiment, a composition may contain two or more AAV stock, each of which expresses a different immunoglobulin construct. In such compositions, the expressed proteins may combine to form a single immunoglobulin or may express two or more immunoglobulins having different targets. These different targets may be to different ligands on the same cell type or the same virus (or other target), or to two completely different pathogens. The compositions are designed for intrathecal delivery. In one embodiment, a spinal tap is performed in which from about 15 mL (or less) to about 25 mL CSF is removed and in which vector is suspended in a compatible carrier and delivered to the subject.

The rAAV, preferably suspended in a physiologically compatible carrier and optionally admixed with one or more excipients, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include Elliot's B, sterile saline, lactose, sucrose, maltose, and water. The selection of the carrier is not a limitation of the present invention. Optionally, the compositions of the invention may contain, in addition to the rAAV and carrier(s), other conventional pharmaceutical ingredients, such as preservatives, or chemical stabilizers.

In one embodiment, the compositions described herein are used in preparing medicaments for treating central nervous system disorders and diseases.

In another aspect, a method for treatment of Alzheimer's Disease is provided which involves intrathecal delivery of an AAV vector composition as described herein, in which at least one AAV vector stock expresses an immunoglobulin specific for a Aβ, beta secretase, and/or the tau protein, to subject in need thereof.

In still another embodiment, a method for treatment of Parkinson's Disease or related synucleinopathies is provide which involves intrathecal delivery of an AAV vector composition as provided herein, in which at least one AAV vector stock encodes one or more leucine-rich repeat kinase 2 antibody, dardarin (LRRK2) antibody, alpha-synuclein antibody, and/or DJ-1 (PARK7) antibody.

In yet a further aspect, a method for treatment of multiple sclerosis is provided herein which involves intrathecal delivery of an AAV vector composition as provided herein, in which composition at least one vector stock encodes an immunoglobulin directed against one or more of an a4-integrin, CD20, CD25, IL12, p40+IL23p40, LINGO-1, CD40, and rHIgM22, CD52, IL17, CD19, and/or SEMA4D.

In yet another aspect, a method for treatment of ALS is provided which involves intrathecal delivery of an AAV vector composition as described herein, in which at least one AAV vector stock expresses an immunoglobulin specific for ALS enzyme superoxide dismutase 1 (SOD1) and variants thereof, a Derlin-1-binding region, and/or an antibody construct against neurite outgrowth inhibitor. In one embodiment, the vector and/or composition comprises an anti-SOD1 immunoglobulin Fc fragment.

In one aspect a method is provided for treatment of prion related diseases which comprises intrathecal delivery of an AAV vector composition, in which at least one vector stock encodes an immunoglobulin directed one or more of major prion protein, or PrPSc.

Animal models for assessing the effectiveness of a treatment against a variety of the disorders and diseases described herein are available. See, e.g., animal models for assessing Alzheimer's disease described, e.g., in D Van Dam and P. P. De Deyn, Br J Pharmacol, 2011 October; 164(4): 1285-1300. Models for assessing Parkinson's disease drugs have also been described, e.g., in HT Tran et al, Cell Reports, Vol. 7, Issue 6, p 2054-2065, Jun. 26, 2014, R M Ransajoff, Nature Neuroscience, August 2012, Vol 15, 1074-1077 (multiple sclerosis); M. A Pouladi et al, Natuer Reviews Neuroscience, 14, 708-721 (2013) (Huntingdon's disease); N Femandez-Borges, et al., Cur top Med Chem 2013; 13(19): 2504-21 (anti-prion drugs); PMcGoldrick, et al, Biochimica et Biophysica Acta (BBA)-Molecular Basis of Disease, Vol. 1832, Issue 9, September 2013, pp. 1421-1436 and J M Moser et al, Mol Genet Genomics, 2013 June; 288(5-6): 207-29 (ALS). Still other models are known to those of skill in the art.

In another aspect, a method for treatment of infectious disease of the central nervous system is provided which involves intrathecal delivery of an AAV vector composition as provided herein, in which composition at least one vector stock encodes an immunoglobulin directed against the pathogen which causes said infectious disease. Examples, without limitation, include one or more immunoglobulins directed against one or more of *Mycobacterium tuberculosis* (tuberculosis), *Neisseria meningitides* (meningitis), *Streptococcus pneumonia, Listeria monocytogens* (listeriosis), *Borrelia burdorferia* (lyme disease), human deficiency virus (acquired immunodeficiency syndrome), a herpes family viruses, varicella zoster virus, Epstein-Barr virus (EBV), cytomegalovirus, and/or JC virus.

Optionally, the AAV compositions as described herein are administered in the absence of an additional extrinsic pharmacological or chemical agent, or other physical disruption of the blood brain barrier.

In a combination therapy, the AAV-delivered immunoglobulin construct described herein is administered before, during, or after commencing therapy with another agent, as well as any combination thereof, i.e., before and during, before and after, during and after, or before, during and after commencing therapy The compositions described herein may be used in a regimen involving co-administration of other active agents. Any suitable method or route can be used to administer such other agents. Routes of administration include, for example, systemic, oral, intravenous, intraperitoneal, subcutaneous, or intramuscular administration. Optionally, the AAV compositions described herein may also be administered by one of these routes.

The following examples are illustrative only and are not a limitation on the invention described herein.

EXAMPLES

Example 1: CNS Expression of AAV9-Mediated Delivery of Anti-SIV Immunoadhesin To evaluate the potential for long-term antibody production in the CNS following IT AAV delivery, a vector encoding an immunoadhesin was administered to two non-human primates, and the concentration of the transgene product in CSF was evaluated by ELISA. The AAV 9 vector expressing a rhesus macaque derived immunoadhesin (201IA) was constructed as previously described for AAV8, except the CB promoter (chicken beta actin with cytomegalovirus enhancer) was used in place of the cytomegalovirus promoter [Greig J A, et al. (2014) Intramuscular Injection of AAV8 in Mice and Macaques Is Associated with Substantial Hepatic Targeting and Transgene Expression. PLoS ONE 9(11): e112268] and the AAV9 capsid substituted for AAV8.

Briefly, the codon-optimized nucleotide sequence for rhesus macaque anti-SIV mac251 gp120 IgG-201 (Glamann et al. J Virol. 1998; 74(15):7158-7163. doi: 10.1128/JVI.74.15.7158-7163.2000.Updated.) immunoadhesin (201IA) was cloned into an AAV expression construct. The construct was flanked by AAV2 inverted terminal repeats and contained a CB7 promoter, a chimeric intron, and a rabbit globin polyadenylation sequence (pAAV.CB7.CI.201IA.rBG). The sequence of this plasmid was confirmed [SEQ ID NO: 1 (SEQ ID NO: 2 corresponds to encoded 201IA sequence)].

The rAAV9.CB7.CI.201IA.rBG vector ($3\times10^{12}$ GC/kg) was delivered into the cerebrospinal fluid (CSF) of two cynomolgus macaques (IDs 0411 and 9860) by suboccipital puncture. Serum and CSF were collected periodically following vector administration. The concentration of 201IA in CSF and serum were determined by ELISA as follows.

All procedures were conducted at room temperature unless indicated otherwise. Plates were washed with BioTek 405TS microplate washer using PBS+0.05% Tween-20. mac251 gp120 (Immune Technology Corp.) diluted to 2 μg/mL in PBS was incubated overnight on Costar® 96-well EasyWash™ ELISA assay plates (Corning) at 4° C. Plates were then blocked 201IA ELISA blocking buffer (PBS+5% heat-inactivated fetal bovine serum+1 mM EDTA+0.07% Tween-20). Diluted samples were added to plates and diluted 2-fold down the plate at least four times. Plates were incubated for 1 h at 37° C. and blocked again in 201IA ELISA blocking buffer. Plates were then incubated with AffiniPure polyclonal goat anti-human IgG-biotin (Jackson ImmunoResearch Labs) diluted in PBS then with streptavidin-horseradish peroxidase (Abcam) diluted in PBS. 3,3',5,5'-tetramethylbenzidine (TMB) substrate was used to develop the plates. After stopping the colorimetric reaction with $H_2SO_4$, plates were read using a SpectraMax M3 (Molecular Devices) plate reader at 450 nm.

The results for each of the two animals are illustrated in FIGS. 1A and 1B, which show the concentration of 201IA in cerebrospinal fluid and serum, respectively from administration to day 400 post-dose. The concentration scale for CSF is presented in ng/mL, whereas expression levels in serum were measured in micrograms (μg)/mL.

Example 2—I253A Mutation of 201IA to Abrogate FcRn Binding

A nucleotide sequence 768 bp in length complementary to the 201IA gene but containing a mutation corresponding to I253A or H453A of the heavy chain amino acid sequence (Kabat numbering) was obtained from GeneArt (Life Technologies). The sequence was flanked by Pst1 and BstZ17I restriction sites matching those in pAAV.CB7.CI.201IA.rBG. The mutated sequences were separately cloned into a pAAV.CB7.CI.201IA.rBG by restriction digest using the enzymes indicated (NEB) and ligation (TaKaRa Inc.) as described by the manufacturers. Sanger sequencing (GeneWiz) was used to confirm complementarity of pAAV.CB7.CI.201IA.rBG [SEQ ID NO: 1 (SEQ ID NO: 2 corresponds to encoded 201IA sequence)], pAAV.CB7.CI.201IA(I253A).rBG [SEQ ID NO: 3 (encoding SEQ ID NO:4)] and pAAV.CB7.CI.201IA(H435A).rBG [SEQ ID NO: 5 (encoding SEQ ID NO:6] on either side of the desired mutation.

AAV9 vectors are generated using these plasmids using the methods described in Example 1.

Example 3—Generation Exemplary AAV.scFv Constructs

Three illustrative scFv constructs were prepared. These constructs were designed to eliminate the Fc region while still binding to the full-length anti-amyloid beta (Aβ). These constructs were designed to reduce the risk of amyloid related imaging abnormalities and/or to limit the exposure of vessels to high monoclonal antibody concentrations.

A. Aducanumab scFv

The full-length antibody has been described as targeting fibrillary Aβ [Weiner et al, Nature Reviews, Immunology, 6: 404-416 (May 2006)]. To generate the scFv, the amino acid sequences of the variable heavy (aa 21-143 of SEQ ID NO: 8) and variable light domains (aa 159-265 of SEQ ID NO: 8) of a recombinant, fully human anti-Aβ IgG mAb (aducanumab, Biogen) were identified based on the WHO-published sequence [International Nonproprietary Names for Pharmaceutical Substances (INN), WHO Drug Information, Vol 27, No. 4, 2013, p401-402; see, also WO 2014/089500A1], which were codon optimized while being reverse translated to a nucleic acid sequence. The heavy and light domains were connected with a nucleic acid sequence encoding Gly-Ser linker (GGGGSGGGGSGGGGS, as 144-158 of SEQ ID NO: 8). A coding sequence for an IL-2 secretion signal peptide (aa 1-20 of SEQ ID NO: 8) was fused to the 5' end of the nucleic acid sequence, and a coding sequence for 6×His tag was placed on the 3' end of the nucleic acid to facilitate purification. These sequences designed by us were ordered from and synthesized by a commercial contract facility. The plasmid contains, among other plasmid elements, an AAV vector genome consisting of: SEQ ID NO: 13: a 5' AAV2-ITR, a CMV IE promoter, a CB promoter, a chicken beta-actin intron, the scFV sequence, a rabbit beta-globin polyA, and an AAV2-3' ITR. This plasmid was co-expressed with a plasmid expressing the AAV9 capsid in the packaging 293 cell line. Also co-expressed in the packaging 293 cell line were the AAV rep functions and adenovirus helper functions required to package the AAV genome containing the scFV coding sequence and other regulatory elements flanked by the AAV ITRs into the AAV9 capsid. The resulting recombinant vector has an AAV9 capsid and the packaged AAV vector genome [SEQ ID NO: 13], termed AAV9.CB7.CI.aducanumabscFv.rGB.

In the study described herein, vector yield as determined by digital droplet PCR (ddPCR) was $5.89\times10^{13}$ genome copies (GC/mL). Vector lots were assessed using the ddPCR techniques for determining AAV vector genome titers by ddPCR in M. Lock et al, Hu Gene Therapy Methods, Hum Gene Ther Methods. 2014 April; 25(2): 115-25. doi: 10.1089/hgtb.2013.131. Epub 2014 Feb. 14.

B. Crenezumab scFv

Crenezumab is a recombinant humanized monoclonal antibody against human 1-40 and 1-42 Aβ (also termed β-amyloid) developed by AC Immune and licensed to Genentech. Crenezumab is also knows at MABT5102A. It is characterized by having HVR region sequences of FIG. 2 of WO 2015/120233A1, and sequences of SEQ ID NO: 2-9, therein. The antibody has been described as being capable of targeted the oligomeric, soluble, and fibrillary Aβ.

The crenezumab scFv was prepared as described above for aducanumab, substituting the amino acid sequences of the variable heavy [aa 21-131 of SEQ ID NO: 10] and variable light chains [aa 147-258 of SEQ ID NO: 10] of crenezumab which were synthesized based on the WHO-published sequence [International Nonproprietary Names for Pharmaceutical Substances (INN), WHO Drug Information, Vol 25, No. 2, pp. 163-164 (2011); see, also WO 2015/120233A]. The resulting recombinant vector has an AAV9 capsid and the packaged AAV vector genome [SEQ ID NO: 14], termed AAV9.CB7.CI.crenezumabscFv.rGB.

In the study described herein, vector yield as determined by ddPCR was $3.79 \times 10^{13}$ GC/mL. Vector lots were purified and assessed using ddPCR as described, M. Lock et al, Hu Gene Therapy Methods, Hum Gene Ther Methods. 2014 April; 25(2):115-25. doi: 10.1089/hgtb.2013.131. Epub 2014 Feb. 14.

C. Solanezumab scFv

Solanezumab is a recombinant humanized monoclonal antibody available from Eli Lilly. Although it has been described as being highly homologous to crenezumab, it targets only the soluble Aβ, whereas crenezumab targets the oligomeric, soluble and fibrillar Aβ. Solanezumab is characterized by having HVR region sequences of U.S. Pat. No. 7,195,761. The sequences used to construct the scFV was obtained from International Nonproprietary Names for Pharmaceutical Substances (INN), WHO Drug Information, Vol. 23, No. 3, pp. 263-264 (2009).

The solanezumab scFv was prepared as described above for aducanumab, substituting the amino acid sequences of the variable heavy [aa 21-131 of SEQ ID NO: 12] and variable light chains [aa 147-258 of SEQ ID NO: 12] of solanezumab which were synthesized based on the WHO-published sequence [International Nonproprietary Names for Pharmaceutical Substances (INN), WHO Drug Information, Vol 25, No. 2, pp. 163-164 (2011); see, also WO 2015/120233A]. The resulting recombinant vector has an AAV9 capsid and the packaged AAV vector genome [SEQ ID NO: 15], termed AAV9.CB7.CI.solanezumabscFv.rGB.

In the study described herein, ddPCR yield was $5.25 \times 10^{13}$ GC/mL. Vector lots were purified and titered by ddPCR as described.

D. ELISA to Detect Anti-Aβ scFvs

The scFv expression plasmids of Parts A-C above were used to produce the ELISA standards prior to packaging the plasmid in the AAV9 capsid. To purify the scFv ELISA standards, the pAAV plasmid were transfected into 293 cells. The scFvs were secreted into the cell culture supernatant. Taking advantage of the His-tag on the end of the scFvs, the scFvs were purified by running the supernatant over a His-trap column [GE Healthcare]. The remainder of the supernatant flows through the column. The bound His-tagged material (scFvs) was then eluted using a high-salt buffer.

The following enzyme linked immunsorbent assay (ELISA) was used to detect anti-Aβ scFvs. The plate is coated with 1 µg/mL recombinant human amyloid beta at 4° C. overnight, using the "mixed-species" amyloid (aggregated and monomeric forms of the peptide). The assay is performed as follows. Wash 5× with PBS+0.05% Tween-20. Block with PBS+1% bovine serum albumin for 1 hour at room temperature. Add serum/brain lysate/purified anti-Aβ scFvs. The three scFvs described in Parts A, B and C of this example were constructed with a His tag to facilitate the ELISA analysis, and they were purified from 293 supernatant using a His-trap column [His-Trap FF 1 ml column, GE Healthcare] according to manufacturer's instructions [www.gelifesciences.com]. Incubate at 37° C. for one hour. Wash 5× with PBS+0.05% Tween-20. Add anti-His tag antibody (AbCam ab1187) diluted 1:10,000 in PBS. Incubate at RT for one hour. Wash 5× with PBS+0.05% Tween-20. Develop with TMB substrate (3,3',5,5'-tetramethylbenzidine) for 30 minutes at RT. Add 2N $H_2SO_4$ to stop reaction. Read at 450 nm and 540 nm on plate reader.

E. Pilot Study for Anti-Aβ scFvs in 3×TG Mouse Model

AAV9.CB7.aducanumabSCFV.RBG, AAV9.CB7.crenezumabSCFV.RBG, AAV9.CB7.solanezumabSCFV.RBG, or PBS are administered intracerebroventricular (ICV) to 6 week-old 3×TG mice (MMRRC Repository/Jackson) [See. e.g., R. Sternicdzuk, et al, "Characterization of the 3×Tg-AD mouse model of Alzheimer's disease: part 2. Behavioral and cognitive changes". Brain Res. 2010 Aug. 12; 1348:149-55. doi: 10.1016/j.brainres.2010.06.011. Epub 2010 Jun. 15 and R. Sterniczuk, et al, "Characterization of the 3×Tg-AD mouse model of Alzheimer's disease: part 1. Circadian changes.", Brain Res. 2010 Aug. 12; 1348:139-48. doi: 10.1016/j.brainres.2010.05.013. Epub 2010 May 31.] at $1 \times 10^{11}$ gc/mouse, 6 mice per dosing cohort. Control mice (do not develop Alzheimer's pathology): B6129SF2/J (Jackson). Serum is taken monthly to monitor scFv expression. Mice undergo Morris water maze and/or Y-maze alternation behavioral testing at 6 months post-vector administration [See, e.g., Webster et al. Using mice to model Alzheimer's dementia: an overview of the clinical disease and the preclinical behavioral changes in 10 mouse models. Front Genet. 2014; 5: 88.]. The Morris water maze is designed to measure spatial memory, movement control and cognitive mapping [Whishaw, I. Q. (1995). "A comparison of rats and mice in a swimming pool place task and matching to place task: some surprising differences". Physiology & Behavior. 58 (4): 687-693. doi: 10.1016/0031-9384(95)00110-5; Crusio, Wim (1999). "Methodological considerations for testing learning in mice". In Crusio, W. E.; Gerlai, R. T. Handbook of molecular-genetic techniques for brain and behavior research (1st ed.). Amsterdam: Elsevier. pp. 638-651.]. The Y maze is used for assessing spatial working memory in rats and mice, especially for spontaneous alternation tasks. The maze may be purchases commercially, e.g., from Panlab. Mice are euthanized at 12 months of age for histological evaluation of Aβ pathology and quantification of scFv/amyloid by ELISA from brain lysate. Other preliminary studies examine the efficacy of scFvs in older mice (dosing at ~4-6 months, which is the average age of onset of visible Aβ pathology in this model). Cohorts of mice are dosed at 6 weeks of age and at 4-6 months of age for histological evaluation of tau protein pathology, followed by euthanizing the mice at 15 months of age.

This application contains sequences and a sequence listing, which is hereby incorporated by reference. All publications, patents, and patent applications, including priority U.S. Patent application 62/247,498, filed Oct. 28, 2015, cited in this application are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

TABLE

| SEQ ID NO: (containing free text) | Free text under <223> |
|---|---|
| | (Sequence Listing Free Text) The following information is provided for sequences containing free text under numeric identifier <223>. |
| 1 | <220><br><221> misc_feature<br><222> (275) ... (404)<br><223> 3' ITR (complement)<br><220><br><221> misc_feature<br><222> (3226) ... (3355)<br><223> 5' ITR<br><220><br><221> misc<br><222> (3423) ... (3804)<br><223> CMV IE promoter<br><220><br><221> CDS<br><222> (5161) ... (6690)<br><223> 201IA |
| 3 | <220><br><221> misc<br><222> (1) ... (130)<br><223> 5' ITR<br><220><br><221> misc_feature<br><222> (198) ... (579)<br><223> CMV IE promoter<br><220><br><221> promoter<br><222> (582) ... (863)<br><223> CB promoter<br><220><br><221> Intron<br><222> (958) ... (1930)<br><223> chicken beta-actin intron<br><220><br><221> CDS<br><222> (1936) ... (3465)<br><223> CMV IE promoter<br><220><br><221> polyA_signal<br><222> (3529) ... (3655)<br><223> rabbit globin polyA<br><220><br><221> misc_feature<br><222> (3744) ... (3873)<br><223> 3' ITR (complement)<br><220><br><221> misc_feature<br><222> (4636) ... (5493)<br><223> AP(R) marker |
| 4 | <223> Synthetic Construct |
| 5 | <221> misc_feature<br><222> (275) ... (404)<br><223> 3' ITR (complement)<br><220><br><221> misc_feature<br><222> (3423) ... (3804)<br><223> CMV IE promoter<br><220><br><221> promoter |

TABLE-continued

| SEQ ID NO: (containing free text) | Free text under <223> |
|---|---|
| | (Sequence Listing Free Text) The following information is provided for sequences containing free text under numeric identifier <223>. |
| | <222> (3807) ... (4088)<br><223> CB promoter<br><220><br><221> TATA_signal<br><222> (4061) ... (4064)<br><223> rabbit globin polyA<br><220><br><221> Intron<br><222> (4183) ... (5155)<br><223> chicken beta-actin intron<br><220><br><221> CDS<br><222> (5161) ... (6690)<br><223> CMV IE promoter |
| 6 | <220><br><223> Synthetic Construct |
| 7 | <223> engineered aducanumab scFv coding sequence |
| 8 | <223> Aducanumab scFv construct amino acid sequence<br><220><br><221> SIGNAL<br><222> (1) ... (20)<br><223> IL2 secretion signal<br><220><br><221> MISC_FEATURE<br><222> (21) ... (143)<br><220><br><221> MISC_FEATURE<br><222> (144) ... (158)<br><223> Gly-Ser Llinker<br><220><br><221> MISC_FEATURE<br><222> (159) ... (265)<br><223> Light Variable region<br><220><br><221> MISC_FEATURE<br><222> (266) ... (271)<br><223> 6xHistag (Explasy) |
| 9 | <223> Engineered crenezumab scFv construct |
| 10 | <223> Engineered Crenezumab scFv amino acid sequence<br><220><br><221> SIGNAL<br><222> (1) ... (20)<br><223> IL-2 secretion signal<br><220><br><221> MISC_FEATURE<br><222> (21) ... (131)<br><223> Heavy variable region<br><220><br><221> MISC_FEATURE<br><222> (131) ... (146)<br><223> Gly-Ser Linker<br><220><br><221> MISC_FEATURE<br><222> (147) ... (258)<br><223> Light Variable Region<br><220><br><221> MISC_FEATURE<br><222> (259) ... (264)<br><223> 6xHistag |
| 11 | <223> engineered Solanezumab scFv construct nucleic acid sequence: |
| 12 | <223> engineered Solanezumab scFv construct amino acid sequence<br><220><br><221> SIGNAL<br><222> (1) ... (20)<br><223> IL2 secretion signal<br><220><br><221> MISC_FEATURE<br><222> (21) ... (131) |

TABLE-continued (Sequence Listing Free Text)
The following information is provided for sequences containing free text under numeric identifier <223>.

| SEQ ID NO: (containing free text) | Free text under <223> |
|---|---|
| | <223> Heavy chain variable |
| | <220> |
| | <221> MISC_FEATURE |
| | <222> (132) . . . (146) |
| | <220> |
| | <221> MISC_FEATURE |
| | <222> (147) . . . (258) |
| | <223> Variable Light Region |
| | <220> |
| | <221> MISC_FEATURE |
| | <222> (259) . . . (264) |
| | <223> 6xHistag |
| 13 | <223> AAV vector genome CB7.CI.aducanumabscFvRBG |
| | <220> |
| | <221> repeat_region |
| | <222> (1) . . . (130) |
| | <223> 5" AAV2-ITR |
| | <220> |
| | <221> repeat_region |
| | <222> (198) . . . (579) |
| | <223> CMV IE promoter |
| | <220> |
| | <221> promoter |
| | <222> (582) . . . (863) |
| | <223> CB promoter |
| | <220> |
| | <221> Intron |
| | <222> (958) . . . (1930) |
| | <223> chicken beta actin promoter |
| | <220> |
| | <221> misc_feature |
| | <222> (2002) . . . (2370) |
| | <223> aducanumab heavy variable region |
| | <220> |
| | <221> misc_feature |
| | <222> (2371) . . . (2415) |
| | <223> Gly-Ser Linker |
| | <220> |
| | <221> misc_feature |
| | <222> (2416) . . . (2736) |
| | <223> aducanumab light chain variable |
| | <220> |
| | <221> misc_feature |
| | <222> (2737) . . . (2754) |
| | <223> His Tag |
| | <220> |
| | <221> polyA_signal |
| | <222> (2821) . . . (2947) |
| | <223> Rabbit globulin polya |
| | <220> |
| | <221> repeat_region |
| | <222> (3036) . . . (3165) |
| | <223> 3' ITR |
| 14 | <223> pAAV.CB7.CI.crenezumabScFv.RBG |
| | <220> |
| | <221> repeat_region |
| | <222> (1) . . . (130) |
| | <223> AAV2 - 5' ITR |
| | <220> |
| | <221> repeat_region |
| | <222> (198) . . . (579) |
| | <223> CMV IE promoter |
| | <220> |
| | <221> promoter |
| | <222> (582) . . . (863) |
| | <223> CB promoter |
| | <220> |
| | <221> misc_feature |
| | <222> (1942) . . . (2001) |
| | <223> IL-2 secretion signal |
| | <220> |
| | <221> misc_feature |

TABLE-continued (Sequence Listing Free Text)
The following information is provided for sequences containing free text under numeric identifier <223>.

| SEQ ID NO: (containing free text) | Free text under <223> |
|---|---|
| | <222> (2001) . . . (2334) |
| | <223> crenezumab heavy variable region |
| | <220> |
| | <221> misc_feature |
| | <222> (2335) . . . (2379) |
| | <223> Gly-Ser linker |
| | <220> |
| | <221> misc_feature |
| | <222> (2380) . . . (2715) |
| | <223> crenezumab varalbe region light |
| | <220> |
| | <221> misc_feature |
| | <222> (2716) . . . (2733) |
| | <223> His tag |
| | <223> rabbit globin polyA |
| | <220> |
| | <221> repeat_region |
| | <222> (3015) . . . (3144) |
| | <223> AAV2 - 3' ITR |
| 15 | <223> pAAV.CB7.CI.solanezumabscFv.RBG |
| | <220> |
| | <221> repeat_region |
| | <222> (1) . . . (130) |
| | <223> AAV2 - 5' ITR |
| | <220> |
| | <221> repeat_region |
| | <222> (198) . . . (579) |
| | <223> CMV IE promoter |
| | <220> |
| | <221> promoter |
| | <222> (582) . . . (863) |
| | <223> CB promoter |
| | <220> |
| | <221> Intron |
| | <222> (958) . . . (1930) |
| | <223> chicken beta-actin intron |
| | <220> |
| | <221> misc_feature |
| | <222> (1942) . . . (2001) |
| | <223> IL-2 secretion signal |
| | <220> |
| | <221> misc_feature |
| | <222> (2002) . . . (2334) |
| | <223> solanezumab heavy variable region |
| | <220> |
| | <221> misc_feature |
| | <222> (2335) . . . (2379) |
| | <223> Gly-Ser Linker |
| | <220> |
| | <221> misc_feature |
| | <222> (2380) . . . (2715) |
| | <223> solanezumab light chain variable region |
| | <220> |
| | <221> polyA_signal |
| | <222> (2800) . . . (2926) |
| | <223> rabbit globin polyA |
| | <220> |
| | <221> misc_feature |
| | <222> (3015) . . . (3144) |
| | <223> AAV2 - 3' ITR |

The invention claimed is:

1. A composition for treatment of Alzheimer's Disease, wherein said composition comprises:
at least one recombinant AAV (rAAV) vector stock comprising an AAV capsid which targets a cell of the central nervous system and a vector genome packaged in the AAV capsid, wherein the vector genome comprises AAV inverted terminal repeat sequences and nucleic acid sequences encoding an immunoglobulin operably linked to expression control sequences which direct expression of the immunoglobulin; and a pharmaceutically acceptable carrier and/or an excipient for intrathecal delivery, wherein the immunoglobulin is a single chain variable fragment antibody (scFv), wherein the scFv is the amino acid sequence of SEQ ID NO: 8.

2. A composition useful for treatment of Alzheimer's Disease comprising at least one AAV vector stock comprising an AAV capsid which targets a cell of the central nervous system, the capsid having packaged therein at least one AAV inverted terminal repeat sequence and sequences encoding an immunoglobulin construct operably linked to expression control sequences therefor, wherein the at least one AAV vector stock expresses an immunoglobulin specific for a Aβ protein, and the composition further comprises a pharmaceutically acceptable carrier and/or excipient suitable for intrathecal delivery, wherein the immunoglobulin is a scFv, wherein the scFv is the amino acid sequence of SEQ ID NO: 8.

3. The composition according to claim 1, wherein excipient excludes chemical and physical disruptors of blood brain barrier.

4. The composition according to claim 2, wherein excipients excludes chemical and physical disruptors of blood brain barrier.

5. The composition according to claim 1, wherein the composition further comprises of the pharmaceutically acceptable carrier selected from one or more of Elliot's B, sterile saline, lactose, sucrose, maltose, and water.

6. The composition according to claim 2, wherein the composition further comprises of the pharmaceutically acceptable carrier selected from one or more of Elliot's B, sterile saline, lactose, sucrose, maltose, and water.

7. The composition according to claim 1, wherein the vector genome further comprises a coding sequence for a secretion signal peptide, wherein the secretion signal peptide is interleukin-2 secretion signal peptide and wherein the secretion signal peptide is located at the 5' end of the nucleic acid sequence encoding the immunoglobulin.

8. The composition according to claim 2, wherein sequences further comprises a coding sequence for a secretion signal peptide, wherein the secretion signal peptide is interleukin-2 secretion signal peptide and wherein the secretion signal peptide is located at the 5' end of the sequences encoding the immunoglobulin.

* * * * *